United States Patent
Fallin et al.

(10) Patent No.: US 7,309,340 B2
(45) Date of Patent: Dec. 18, 2007

(54) METHOD AND APPARATUS FOR BONE PLATING

(75) Inventors: T. Wade Fallin, Hyde Park, UT (US); Robert W. Hoy, Paradise, UT (US)

(73) Assignee: MedicineLodge, Inc., Logan, UT (US)

( * ) Notice: Subject to any disclaimer, the term of this patent is extended or adjusted under 35 U.S.C. 154(b) by 672 days.

(21) Appl. No.: 10/601,177

(22) Filed: Jun. 20, 2003

(65) Prior Publication Data

US 2004/0260306 A1      Dec. 23, 2004

(51) Int. Cl.
A61B 17/58    (2006.01)
A61F 2/00    (2006.01)

(52) U.S. Cl. ..................................... 606/104

(58) Field of Classification Search ............ 606/69–71, 606/72, 73, 104
See application file for complete search history.

(56) References Cited

U.S. PATENT DOCUMENTS

| | | | |
|---|---|---|---|
| 4,388,921 A | 6/1983 | Sutter |
| 4,484,570 A | 11/1984 | Sutter |
| 5,053,036 A | 10/1991 | Perren |
| 5,057,111 A | 10/1991 | Park |
| 5,085,660 A | 2/1992 | Lin |
| 5,151,103 A | 9/1992 | Tepic |
| 5,234,431 A | 8/1993 | Keller |
| 5,269,784 A | 12/1993 | Mast |
| 5,364,399 A | 11/1994 | Lowery |
| 5,501,684 A | 3/1996 | Schiapfer |
| 5,520,690 A | 5/1996 | Errico |
| 5,531,746 A | 7/1996 | Errico |
| 5,549,612 A | 8/1996 | Yapp |
| 5,578,034 A | 11/1996 | Estes |
| 5,591,166 A | 1/1997 | Bernhardt |
| 5,601,553 A | 2/1997 | Trebing |
| 5,643,265 A | 7/1997 | Errico |
| 5,681,311 A | 10/1997 | Foley |

(Continued)

FOREIGN PATENT DOCUMENTS

EP      0684017 B1      2/1999

(Continued)

OTHER PUBLICATIONS

Theken, Tether Anterior Cervical Fixation System (Brochure), 2002.

Primary Examiner—Anuradha Ramana
(74) Attorney, Agent, or Firm—David W. Meibos; MedicineLodge Inc.; Barbara Daniels

(57) ABSTRACT

A bone plating system invention is shown comprising a bone plate and bone fasteners. The bone plate has a top portion, a bottom portion, and an interior middle portion. The fastener-retaining passageway extends through the plate. The fastener-retaining passageway comprises an upper portion having an inwardly projecting capture lip. The capture lip has a first diameter. The fastener-retaining passageway also has a middle undercut portion that has a second diameter. The second diameter is larger than the first diameter. The plate also has at least one access channel extending through the capture lip so as to communicate with the interior middle portion of the plate. The fastener comprises a shaft, a fastener engager means extending from, disposed on or coupled with the shaft for engaging bone and a head mounted on the shaft having a radially elastic member.

13 Claims, 19 Drawing Sheets

U.S. PATENT DOCUMENTS

| | | | |
|---|---|---|---|
| 5,735,853 A | 4/1998 | Olerud | |
| 5,902,303 A | 5/1999 | Eckhof | |
| 5,904,683 A | 5/1999 | Pohndorf | |
| 5,931,838 A | 8/1999 | Vito | |
| 5,954,722 A | 9/1999 | Bono | |
| 6,017,345 A | 1/2000 | Richelsoph | |
| 6,030,389 A | 2/2000 | Wagner | |
| 6,117,173 A | 9/2000 | Taddia | |
| 6,139,550 A | 10/2000 | Michelson | |
| 6,152,927 A | 11/2000 | Farris | |
| 6,193,721 B1 | 2/2001 | Michelson | |
| 6,224,602 B1 | 5/2001 | Hayes | |
| 6,228,085 B1 | 5/2001 | Theken | |
| 6,235,034 B1 | 5/2001 | Bray | |
| 6,258,089 B1 | 7/2001 | Campbell | |
| 6,261,291 B1 | 7/2001 | Talaber | |
| 6,315,779 B1 * | 11/2001 | Morrison et al. | 606/69 |
| 6,331,179 B1 | 12/2001 | Freid | |
| 6,342,055 B1 | 1/2002 | Eisermann | |
| 6,383,186 B1 | 5/2002 | Michelson | |
| 6,398,783 B1 | 6/2002 | Michelson | |
| 6,413,259 B1 | 7/2002 | Lyons | |
| 6,416,528 B1 | 7/2002 | Michelson | |
| 6,428,542 B1 | 8/2002 | Michelson | |
| 6,454,771 B1 | 9/2002 | Michelson | |
| 6,506,191 B1 | 1/2003 | Joos | |
| 6,527,776 B1 | 3/2003 | Michelson | |
| 6,533,786 B1 | 3/2003 | Needham | |
| 6,533,789 B1 | 3/2003 | Hall, IV | |
| 6,558,423 B1 | 5/2003 | Michelson | |
| 6,599,290 B2 * | 7/2003 | Bailey et al. | 606/69 |
| 6,602,255 B1 * | 8/2003 | Campbell et al. | 606/69 |
| 6,695,846 B2 * | 2/2004 | Richelsoph et al. | 606/71 |
| 7,001,389 B1 * | 2/2006 | Navarro et al. | 606/71 |
| 7,048,739 B2 * | 5/2006 | Konieczynski et al. | 606/73 |
| 2001/0047174 A1 | 11/2001 | Donno | |
| 2002/0022843 A1 | 2/2002 | Michelson | |
| 2002/0058939 A1 | 5/2002 | Wagner | |
| 2002/0120273 A1 | 8/2002 | Needham | |
| 2002/0128655 A1 | 9/2002 | Michelson | |
| 2002/0151899 A1 | 10/2002 | Bailey | |
| 2002/0183754 A1 | 12/2002 | Michelson | |
| 2002/0183756 A1 | 12/2002 | Michelson | |
| 2002/0183757 A1 | 12/2002 | Michelson | |
| 2002/0188296 A1 | 12/2002 | Michelson | |
| 2003/0045880 A1 | 3/2003 | Michelson | |
| 2003/0078583 A1 | 4/2003 | Biedermann | |
| 2003/0093082 A1 | 5/2003 | Campbell | |

FOREIGN PATENT DOCUMENTS

| | | |
|---|---|---|
| EP | 0897697 A1 | 2/1999 |
| EP | 0767631 B1 | 12/2000 |
| EP | 1106144 A1 | 6/2001 |
| EP | 0683646 B1 | 10/2001 |
| EP | 1169971 A2 | 1/2002 |
| EP | 0951247 B1 | 10/2002 |
| WO | WO 95/35067 | 12/1995 |
| WO | WO 96/08206 | 3/1996 |
| WO | WO 97/22306 | 6/1997 |
| WO | WO 98/34533 | 8/1998 |
| WO | WO 98/51226 | 11/1998 |
| WO | WO 99/05968 | 2/1999 |
| WO | WO 99/21502 | 5/1999 |
| WO | WO 02/098276 | 12/2002 |
| WO | WO 03/028567 A1 | 4/2003 |

* cited by examiner

METHOD AND APPARATUS FOR BONE PLATING

CROSS-REFERENCE TO RELATED APPLICATIONS

Not applicable.

BACKGROUND OF THE INVENTION

1. The Field of the Invention

The present invention relates to the design and method of use of a bone plate and fastener implant and instrumentation system for stabilizing multiple bone segments. In one embodiment of this invention the system aligns and maintains adjacent human cervical vertebrae in a selected spatial relationship during spinal fusion of the cervical spine from the anterior aspect of the vertebrae.

2. Related Technology

The use of fixation plates and fastener systems for the treatment of spinal disorders for fusion of vertebrae has progressed considerably over the past twenty years. These systems usually include bone fasteners and plate systems that stabilize bone segments. The fasteners typically have a head, a shaft and threads that engage with the bone. The bone fasteners are placed by delivery mechanisms into corresponding openings in the plates and then into the bone itself. The fasteners are then firmly tightened to secure the plate to the bone.

A common problem associated with the use of such fixation plates is the tendency of the bone fasteners to back out of the plate under the dynamics of human movement. As a result of backout, bone fasteners may loosen and eventually disengage from the bone plate resulting in poor fixation. Potentially, this loosening of the bone fastener at the bone plate interface may cause the fastener to ultimately work itself out of both the plate and the bone from which it was implanted. This problem is particularly of concern in areas such as the spine where a loose fastener may impinge or interfere with sensitive tissues and bone structures.

Designers of such bone fixation systems have employed various techniques and developed different backout-preventing mechanism in an attempt to overcome the problem of fastener backout. These systems include secondary backout-preventing mechanisms and passive backout-preventing mechanisms. In secondary backout-preventing mechanisms, the bone fastener is first affixed into the bone through an opening in a bone plate. Once the fastener is in place, the secondary backout-preventing mechanism is then activated to secure the fastener to the plate. These secondary backout-preventing mechanisms comprise devices that are activated independently from the mechanism used to place the fastener. These mechanisms include secondary locking screws, locking collars, deformable tabs or other secondary locking devices that hold the bone fasteners in place after deployment within the plate and bone. The secondary backout-preventing mechanisms are typically independently activated in such ways that the mechanism limits the movement of the head of the bone fastener with the plate. This results in the fasteners being restrained by both the plate and the bone, thus lessening the likelihood of fastener backout.

For example, some designs found in the related art disclose an anterior cervical plating system incorporating an independent locking screw that engages the head of a bone fastener to secure the cervical plate to the vertebra. The locking screw, positioned above the bone fastener after the bone fastener is placed, provides a rigid fixation of the fasteners to the plate.

Other examples of designs found in the related art of secondary backout-preventing mechanisms include a threaded screw nut for use with a bone fixation system wherein the screw nut is partially insertable into an opening of the fixation plate, from the plate underside, and engages a portion of the bone fastener to thereby secure the bone fastener to the fixation plate after the fastener has been independently placed.

Further examples of designs for secondary backout-preventing mechanisms found in the related art disclose a bone fixation system wherein the head of the bone fastener is hollow and expandable. After the fixation plate is secured to the underlying bone by the hollow head bone fastener, a setscrew is then advanced into the hollow head of the fastener to radially expand the head and thereby secure the head to the fixation plate.

The successful use of such secondary backout-preventing mechanisms in the anterior cervical spine is particularly difficult because of the limited operating space available to the surgeon due to anatomic constraints. The above discussed secondary backout-preventing mechanisms require instrumentation to enter the surgical site and activate the backout-preventing mechanism. The instrumentation needed to activate these secondary backout-preventing mechanisms occupies space in the surgical site. In addition, the implementation of these mechanisms can be technically demanding and time consuming. To address the issues related to the limited space available for tools to activate secondary backout-preventing mechanisms and ease of use of the system, fastener and plate systems have been developed that incorporate passive backout-preventing mechanisms. These passive backout-preventing mechanisms are easier to activate since they typically deploy automatically while the surgeon drives the fastener into the opening in the plate and into the bone segment. Usually, no additional steps are required to fix the fastener to the plate. These systems include designs that lock the fastener to the plate by-either passively overcoming interference between the fastener and the plate or activating a passive spring like mechanism in the plate that locks the fastener to the plate.

For example, a bone fixation system wherein the head of the bone fastener is frustoconical in shape and has a directionally corrugated outer surface, is found in the related art. Wherein each opening in the fixation plate has a complementarily corrugated inner surface and is similarly frustoconical in shape. As the fastener is advanced through the corrugated openings and into the underlying bone, the direction of corrugation in the head and in the plate opening permits the head to be received within the corresponding opening, while inhibiting rotation of the fastener in an opposite direction.

Other passive mechanisms that are designed to prevent backout include a system in which a split ring is premounted and attached to the plate. The split ring in the plate that retains the fastener to the plate by engaging the split ring with a groove in the fastener head, or the top of the fastener head. As the groove or the top of the fastener head aligns with the split ring, the split ring expands then snaps into the groove or over the top of the fastener, preventing the fastener from backing out.

Due to the potentially high loads between the plates and the fasteners, the backout-preventing mechanism retaining force need be maximized. While the above described passive backout-preventing mechanisms found in the related art can restrain the fastener to the plate and limit backout, the force required to overcome these mechanisms is typically small, within the magnitude similar to the force needed to drive the fastener into the backout-preventing mechanism. This is because the backout-preventing mechanisms are deformed by the fasteners as the fasteners are driven into the openings in the plate and deformed again in the reverse direction when the fasteners are removed from the openings in the plate. Thus, the force required to remove the fastener from the plate is similar to the force initially used to insert the fastener. Unfortunately, the backout force that the passive backout-preventing mechanisms are capable of restraining may be less than is clinically required for specific high load conditions.

SUMMARY OF THE INVENTION

It is desirable to have bone plating systems that accomplish one or more or a combination of the following features: a system allowing for easy fastener deployment while eliminating backout, retaining structural integrity, allowing fastener angulations, and improving the surgeon feedback when the fastener is deployed in the plate.

One embodiment of the invention is an assembly comprised of a plate and fasteners sized to secure bone fragments. The plate has retaining passageways into which the fasteners pass. The assembly has a passive backout-preventing mechanism incorporated into the fastener that engages with the retaining passageway in the plate. This causes the fastener to be restrained by the retaining passageway. A secondary unloading mechanism is used to deactivate the backout-preventing mechanism allowing removal of the fastener from the plate.

The fastener has a radially elastic compressible member on its head. This radially elastic compressible member becomes smaller in diameter as it is compressed radially, and larger in diameter as its radial compression is relaxed. The plate has a chamfer on the top surface of the retaining passageway to facilitate compression of the radially elastic compressible member as the fastener enters the plate.

Retaining passageways are positioned through the plate in orientations that address specific orthopedic disorders. The functional diameter of the retaining passageway changes from the top of the plate to the bottom of the plate. Near the top of the plate, the functional diameter of the retaining opening is smaller than the uncompressed or relaxed diameter of the fastener head. In the middle portion of the plate, the functional diameter of the retaining passageway transitions to an undercut that is larger than the functional diameter of the retaining passageway near the top of the plate. This provides an area for the head to expand into. Near the bottom of the plate, the functional diameter of the retaining passageway is smaller than that of the functional diameter of the undercut in the middle portion of the plate. This prevents the head of the fastener from passing through the bottom of the plate.

As the radially elastic compressible fastener head is driven into the opening, it is radially compressed by the chamfer on the top portion of the retaining passageway to a diameter small enough to clear the top of the opening. Because the fastener head is radially elastic- and compressible, it is designed to elastically decompress and expand radially once it is placed in the undercut. When the fastener head is positioned in the undercut portion of the retaining passageway, it expands and its movement is restricted by the geometry of the undercut.

In a second embodiment, the fastener head has an incorporated retaining ring on its periphery that acts as the radially elastic compressible member. The retaining ring is incorporated into the fastener head and is positioned on the fastener in a circumferential groove that is also incorporated into the fastener head. The retaining ring is radially compressed as the fastener is driven into the opening in the plate. Once the retaining ring enters the undercut of the opening in the plate, it partially relaxes expanding and catching the underside of the undercut. This restrains the fastener from backing out of the plate.

To remove the fastener from the plate, the retaining ring is radially compressed, by an independent, secondary removal tool, to a smaller diameter size that allows the fastener head to clear the functional diameter of the retaining passageway near the top of the plate. As the retaining ring is compressed, the fastener is removed from the retaining passageway in the plate. The plate has access channels positioned around the periphery of the retaining passageways to facilitate the use of a tool used to remove the restrained fasteners and to facilitate visualization of the locked retaining ring so that the surgeon has visual feedback indicating that the mechanism is activated. These access channels allow space for prongs on the distal end of the removal tool to enter through the top of the plate and engage with the fastener head and radially compress the retaining member while the retaining ring is still positioned in the undercut of the middle portion of the plate.

In one alternate embodiment of the plate and fastener system, the circumferential groove on the periphery of the fastener head is substantially greater in height than the height of the retaining ring. This allows for a variable angle fastener in which the fastener head is retained from backout by the undercut in the retaining passageway, but is still able to toggle due to the clearance between the retaining ring height and height of the groove on the fastener head. This is to facilitate fastener angulation or toggle relative to the plate for variable angle fasteners. The variable angle fasteners also have variable angular position by having a shaft outside diameter that is smaller than functional diameter of the opening near the bottom of the plate. However to limit the load on the retaining ring, the shaft impinges the opening near the bottom of the plate before the retaining ring contacts the top of the undercut in the plate.

In a further embodiment of the plate and fastener system, the circumferential groove on the periphery of the fastener head is closer to the height of the retaining ring than it is in the previously described first fastener embodiment. This allows for fasteners that are more fixed in angulation. The fastener toggles less due to the lessened clearance between the retaining ring height and height of the circumferential groove on the fastener head. The fixed fasteners also maintain angular position by having a shaft outside diameter that closely matches the functional diameter of the opening near the bottom of the plate.

Thus, the type of fastener fixation, fixed or variable angled, can be determined by differences in the diameter of the shaft and the groove in the fastener head, and not differences in the diameters of the plate passageway design. All of the retaining passageways in the plate are similar and can potentially facilitate either a fixed fastener or a variable angle fastener with the only functional difference between the two types of fasteners being the geometry of the head and the shaft. Depending on the clinical situation, the surgeon can determine if a fixed or a variable fastener is required after the plate has been placed, and use the design of fastener that is most clinically appropriate.

DETAILED DESCRIPTION OF THE PREFERRED EMBODIMENTS

Figure 1:
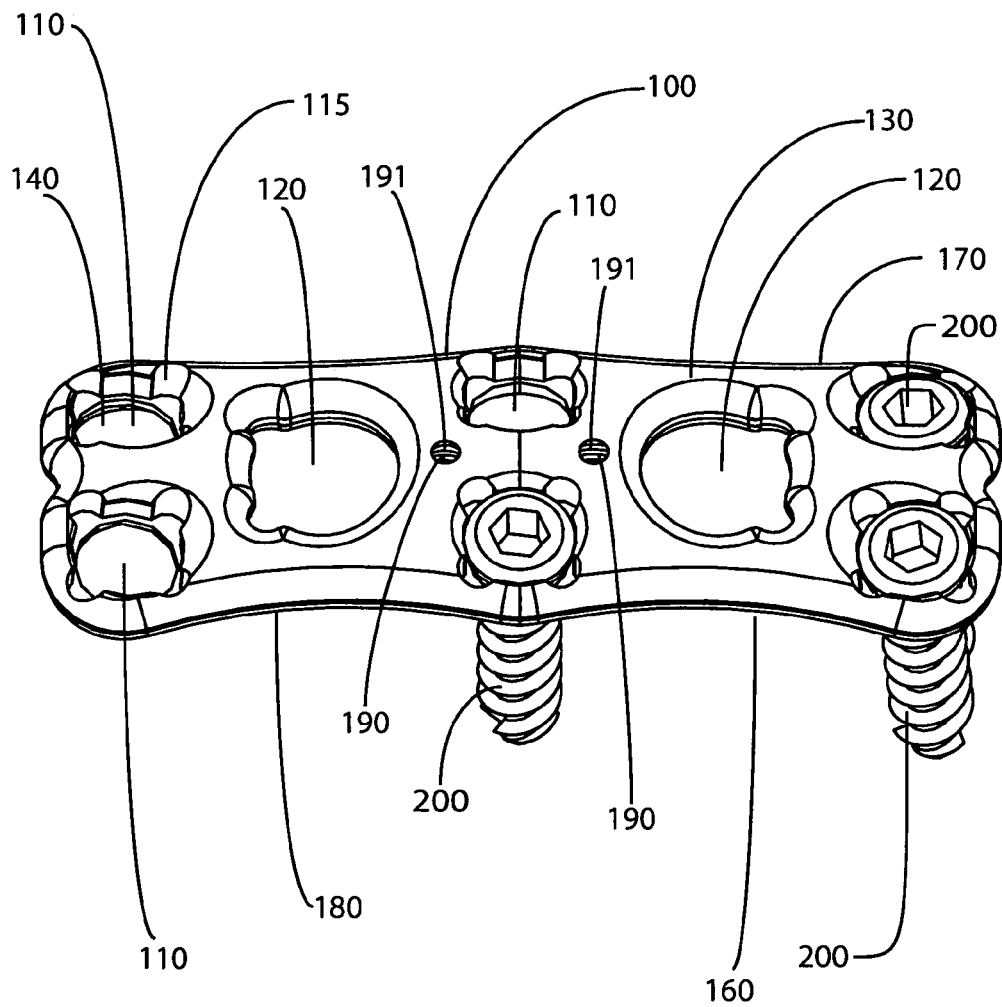
FIG. 1 is a perspective view of a bone plate and fastener system that shows three fasteners retained in the retaining passageways and three additional retaining passageways without fasteners retained.

Depicted in FIGS. 1 through 6B are different embodiments of a plate 100 and fastener 200 system for stabilization of sections of bone. As shown in FIG. 1, the plate 100 comprises a plurality of fastener-retaining passageway 110, a plate top 130, a plate bottom 160, a plate outside periphery 170, a plate interior portion 180, and tissue-access openings 120. The fastener-retaining passageway 110 is configured such that the axial movement of a fastener 200 is restricted-and the angular variability of the fastener 200 is limited when the fastener 200 is placed in the fastener-retaining passageway 110. The number of fastener-retaining passageways 110, their orientation and position are dependent upon the clinical indication for the plate 100 and fastener 200 system. As shown in the embodiment depicted in FIG. 1, the plate 100 may have multiple rows of fastener-retaining passageways 110 adapted to retain multiple fasteners 200, and multiple tissue-access openings 120 adapted to access and visualize tissue through the plate 100. Also shown in FIG. 1 is a plate holding feature 190.

Figure 2:
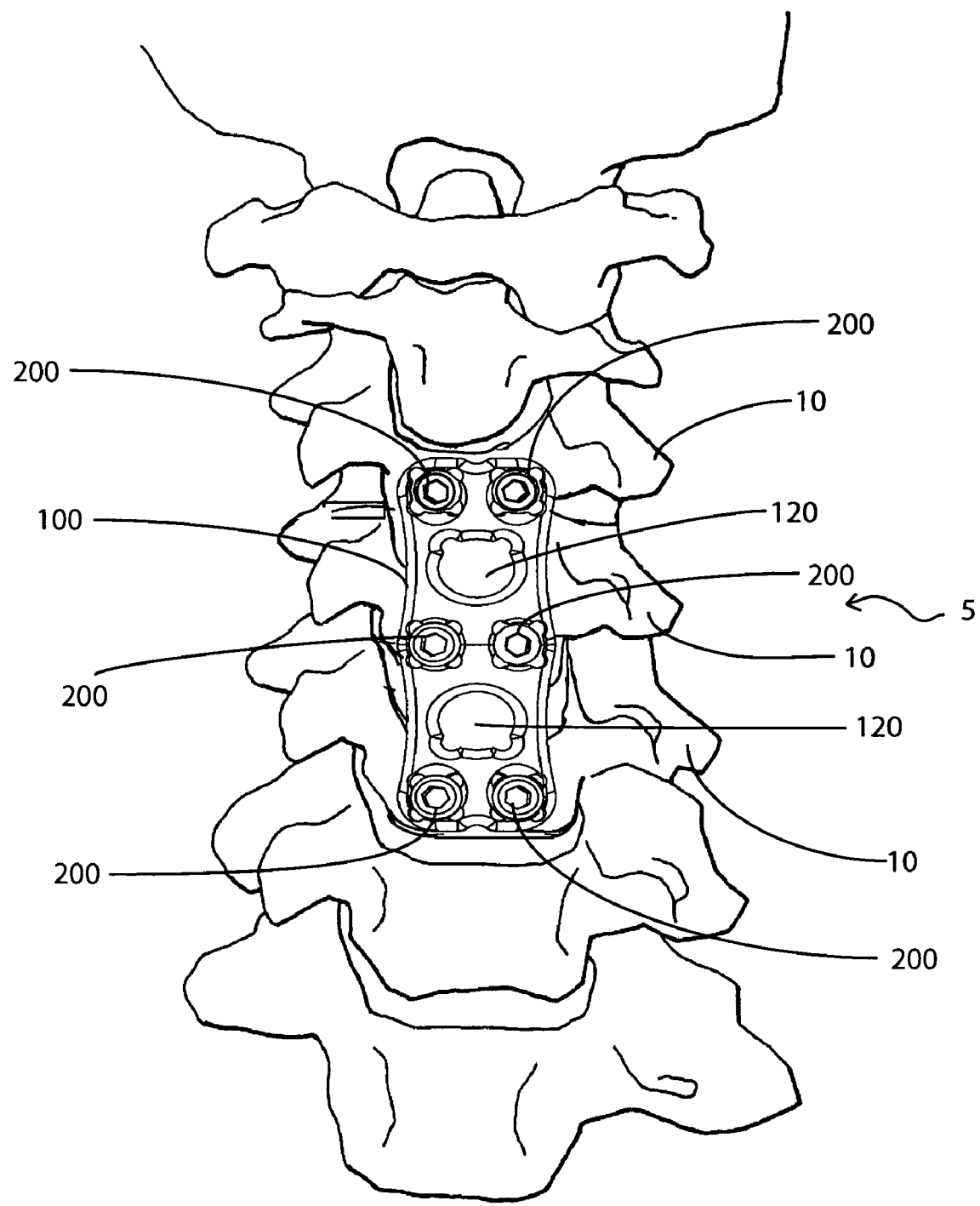
FIG. 2 is an anterior view of a bone plate and fastener system positioned in a cervical spine for use as a vertebra stabilization plate for spinal joint fusion showing six fasteners engaged with three vertebrae and one contiguous plate.

As shown by example in FIG. 2, multiple rows of the fastener-retaining passageways 110 allow for the plate 100 and fastener 200 system to be adaptable for use in spinal vertebrae 10 stabilization. In this example, the plate 100 and fastener 200 system stabilizes the vertebrae 10 in rigid position relative to each other to allow fusion of a section of the cervical spinal column 5. This specific example of the plate 100 and fastener 200 system, used to stabilize vertebrae 10 for spinal fusion, is only one of its many indications for use. Other indications may require the plate 100 to be configured differently but comprise of the same basic features. For stabilization of complex bone segments such as those found in the cervical spinal column 5, multiple rows of the fastener-retaining passageways 110 and the fasteners 200 are preferred. However the plate 100 and fastener 200 system may be comprised of as few as one of the fastener-retaining passageways 110 and one fastener 200 if the plate 100 and the fastener 200 systems is used to stabilize a long bone fracture such as a femoral fracture or a tibial fracture. Likewise, the plate 100 and the fastener 200 systems may be comprised of two rows of the fastener-retaining passageways 110 and two rows of fasteners 200 to stabilize two bone sections. The versatility of the design of the plate 100 and the fastener 200 system allows the surgeon to select-the plate 100 that best fits the surgical need.

As also shown in the embodiment in FIG. 1, the plate 100 may also have a plurality of the tissue-access openings 120. The tissue-access opening 120 allows the surgeon to visualize the tissue or implant materials placed between, on or near the bone segments being stabilized. The tissue-access opening 120 also provides a place for the surgeon to access the tissue between bone segments to manipulate the tissue, or perform other procedures such as adding bone grafts, bioengineered materials or pharmaceuticals to stimulate bone healing. More than one of the tissue-access openings 120 may be positioned between the fastener-retaining passageways 110. The shape of the tissue-access opening 120 is dependent on the clinical indication and the surgical instruments used through the opening. The tissue-access opening 120 may also be shaped such that it provides a feature or features to which an instrument (not shown) can be attached to hold onto the plate 100 during plate 100 insertion and manipulation.

The plate 100 has a plate bottom 160 that is configured to approximate the surface of the bone that is being stabilized.

The plate bottom 160 is typically concave in both its long axis and short axis. However, for bone fixation applications involving complex bone morphology, such as stabilization of pelvis fractures or skull bone fractures, the plate bottom 160 may be concave in one axis and convex in the other, or convex in both the long axis and the short axis, or twisted in either axis, or formed into any complex surface required for a specific procedure. For the embodiment shown in FIG. 2 in which the plate 100 is configured to stabilize vertebra in the cervical spinal column 5, the curvature along the long axis of the plate corresponds to the natural lordotic curvature of the cervical spine while the curvature along the plate's short axis corresponds to the medial-lateral curvature of a vertebral body. In the case of the plate 100 configured to stabilize a cervical spinal column 5, the plate 100 is typically formed with both the lordotic curvature and the medial-lateral curvature concaved to address the normal anatomy of the cervical spinal column 5. However a surgeon can interoperatively bend the plate 100 with special instruments (not shown) to the shape that best fits the patient's anatomy.

The embodiment of the plate holding feature 190 shown in FIG. 1 is a female threaded hole 191 that is dimensioned to receive a male threaded holder instrument (not shown). Other ways of holding on the plate with a holding instrument can be incorporated into the design. The plate holding member 190 can also be a protruding male thread that is adapted to receive a female threaded holder. It may also be non-threaded holding member such as an interference fit, a bayonet connection, a radially expanding collet connection or connection mechanisms commonly know in the art.

Figure 3:
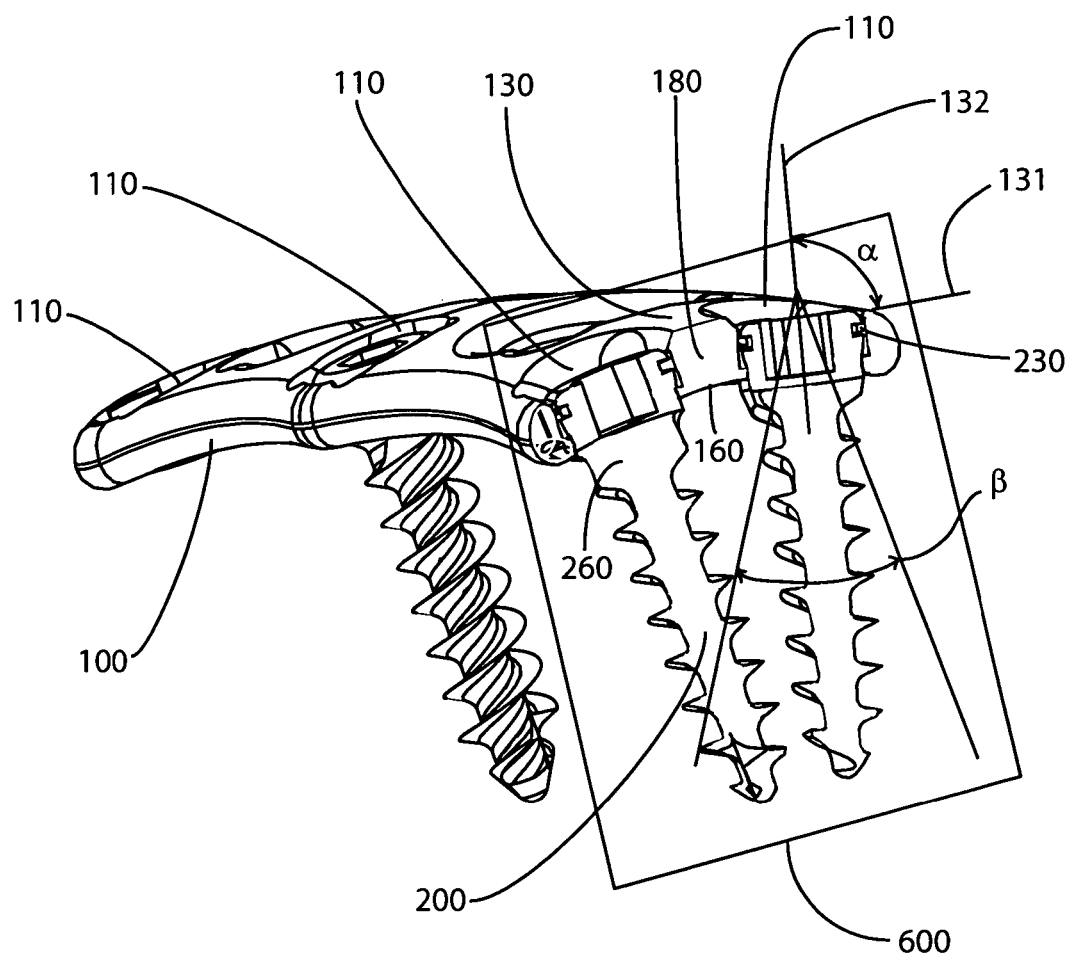
FIG. 3 is a perspective view showing a bone plate and fasteners cut by a cross-sectional view plane that is aligned with the center of the fasteners.
Figure 4A:
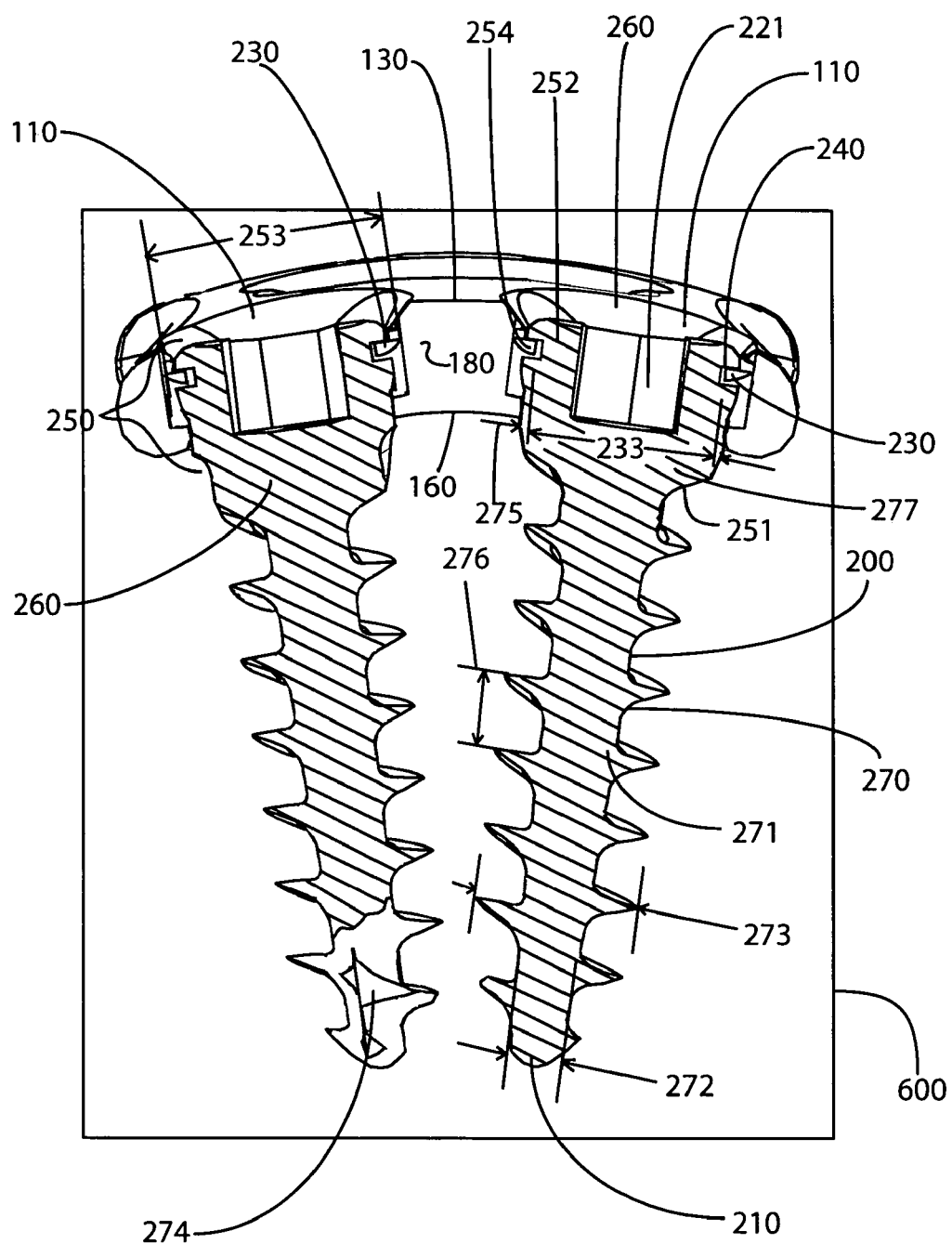
FIG. 4A is a cross-sectional view of the bone plate and fasteners shown from the perspective of the cross-sectional view plane of the of FIG. 3.

FIGS. 3 and 4A show a cross-sectional view plane 600 cutting through the plate 100 and fastener 200 interfaces. The cross-sectional view plane 600 is for visualization purposes to show the details of the interface. FIG. 3 is a perspective view showing the plate 100 and two of the fasteners 200 cut by the cross-sectional view plane 600 that is aligned with the center of the fasteners 200. FIG. 4A is a view of the plate 100 and the fastener 200 shown from the perspective of the cross-sectional view plane 600 of FIG. 3.

As shown in FIG. 4A, the fastener 200 has a fastener proximal end 260 with a fastener head 250 having a fastener head diameter 253, a fastener head topside 252, a fastener head underside 251, a fastener head drive member 221 on the fastener proximal end 260 and a retaining ring 230 incorporated into the fastener head 250. The fastener 200 also has a fastener shaft 277 extending distally from the fastener head 250, with a fastener shaft diameter 275, an elongated fastener engager 270 extending distally from the fastener shaft 277, and a fastener distal tip 210 that is distal to the fastener engager 270.

Figure 4B:
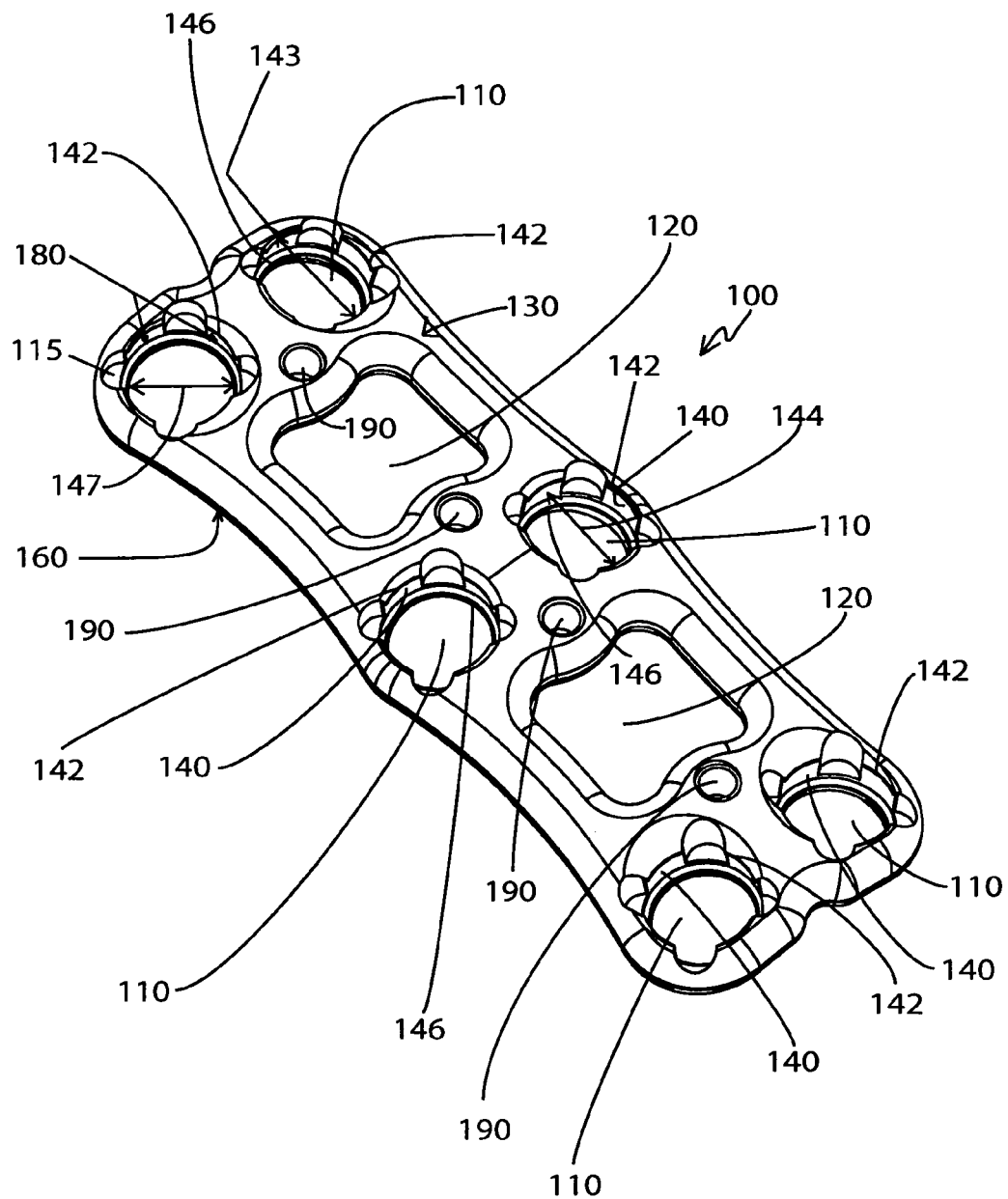
FIG. 4B is a perspective view of the plate.
Figure 5A:
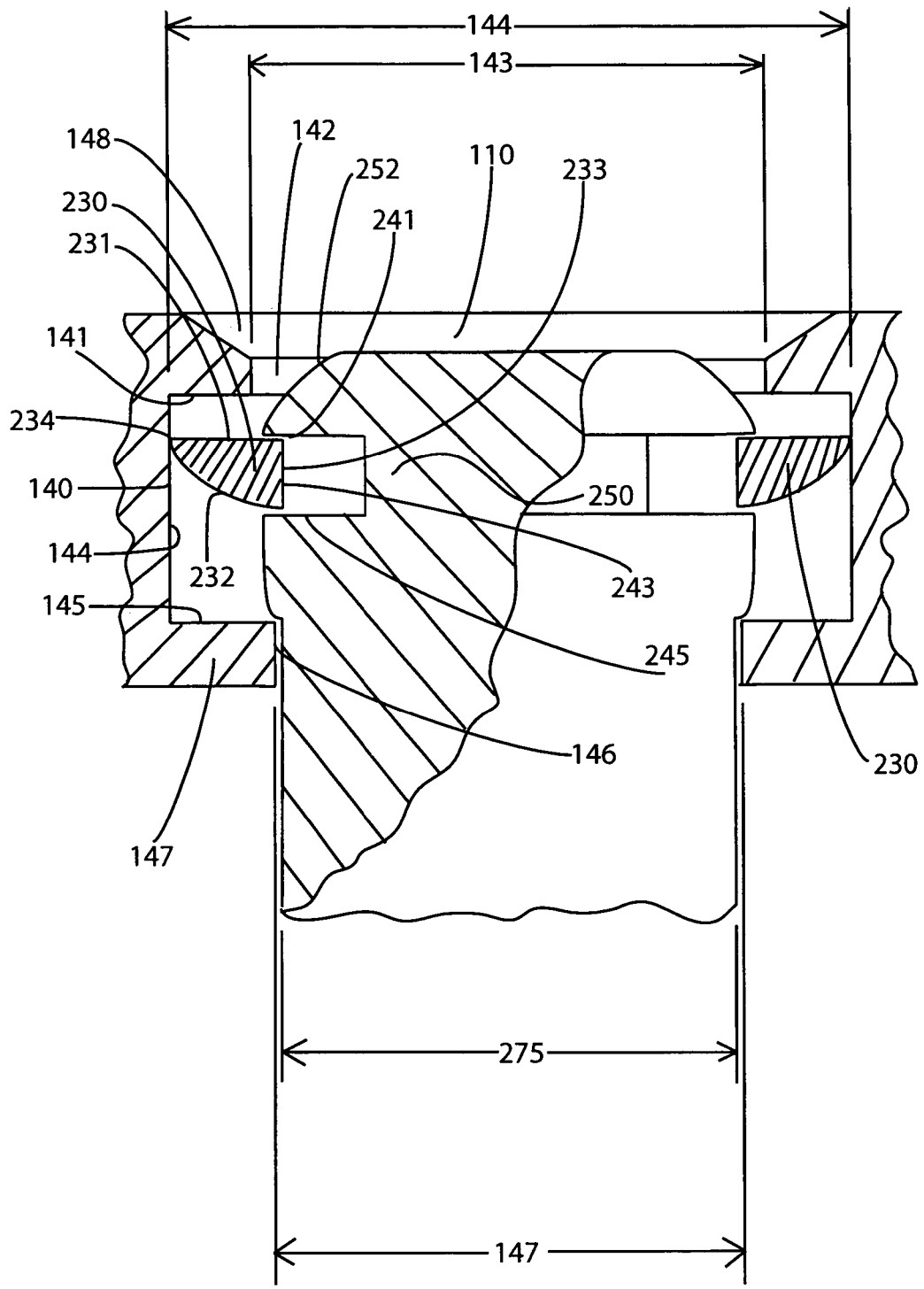
FIG. 5A is a detailed view of the retaining member from FIG. 3 showing the geometry of a variable angle fastener.

As shown in FIGS. 3, 4A, 4B, 5A and 5B, the plate 100 has a fastener-retaining passageway 110 that passes through the plate 100 from the plate top 130 through the plate interior portion 180 to through the plate bottom 160. As shown in FIGS. 4B and 5A, the section of a fastener-retaining passageway 110 that passes near the plate top 130 is a fastener-retaining passageway capture lip 142 with a functional diameter smaller than that of the uncompressed fastener head 250. The maximum diameter that can be passed through the fastener-retaining passageway capture lip 142 is a functional capture lip diameter 143. The section of the fastener-retaining passageway 110 that passes through a plate interior portion 180 is a fastener-retaining passageway undercut 140 with a functional undercut diameter 144 that is larger than that of the functional capture lip diameter 143. The functional undercut diameter 144 is the minimal diameter of the undercut. The section of the fastener-retaining passageway 110 that passes near the plate bottom 160 is the bottom retainer 146 and it has a functional bottom retainer diameter 147 that is smaller than that of the functional undercut diameter 144. This bottom retainer 146 is the area of the plate 100 that restricts the fastener head 250 from passing through the plate 100. The smallest functional diameter of the bottom retainer 146 is the functional bottom retainer diameter 147.

Figure 5B:
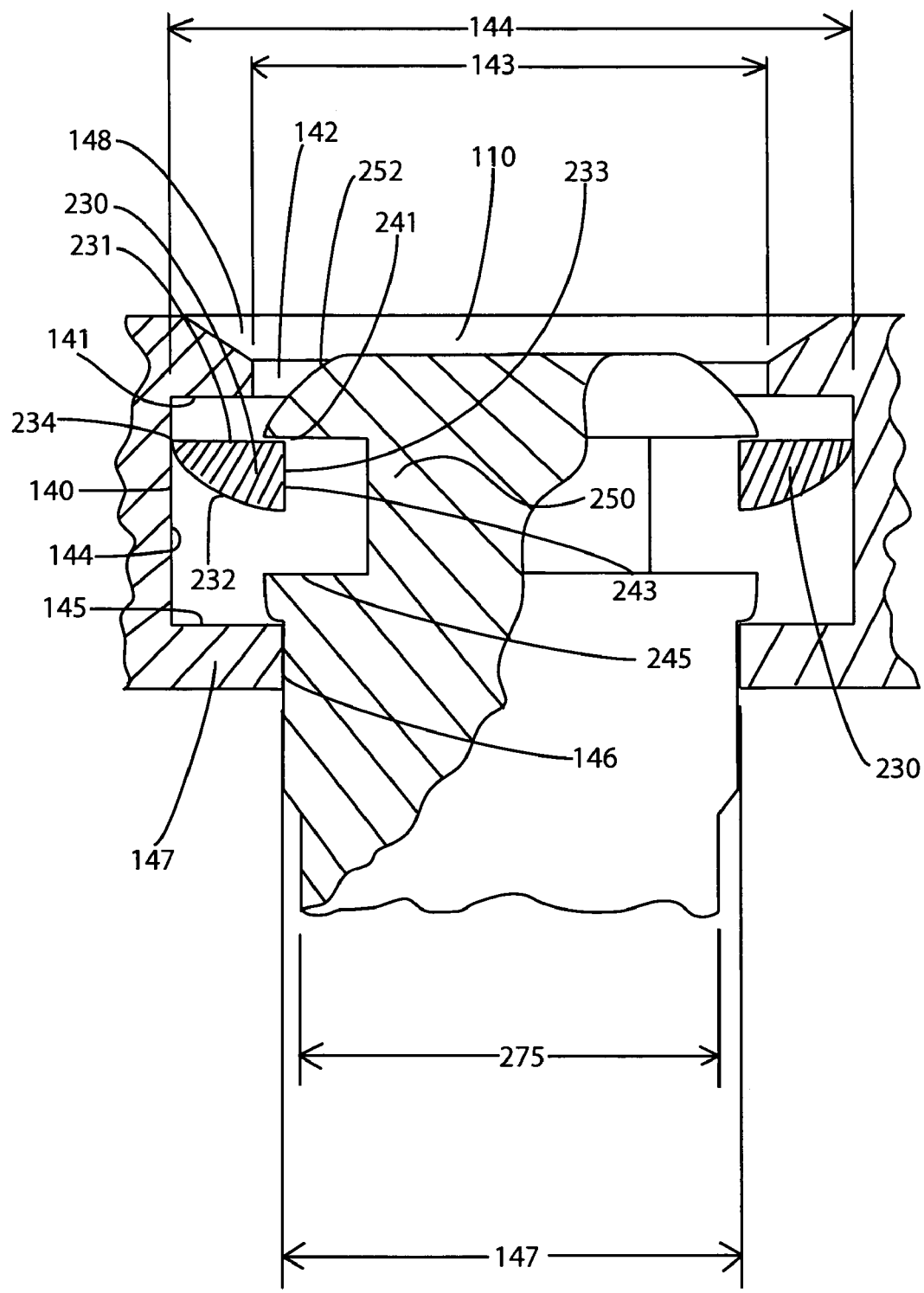
FIG. 5B is a detailed view of the retaining member from FIG. 3 showing the geometry associated with that of a representative fixed angle fastener design.
Figure 6A:
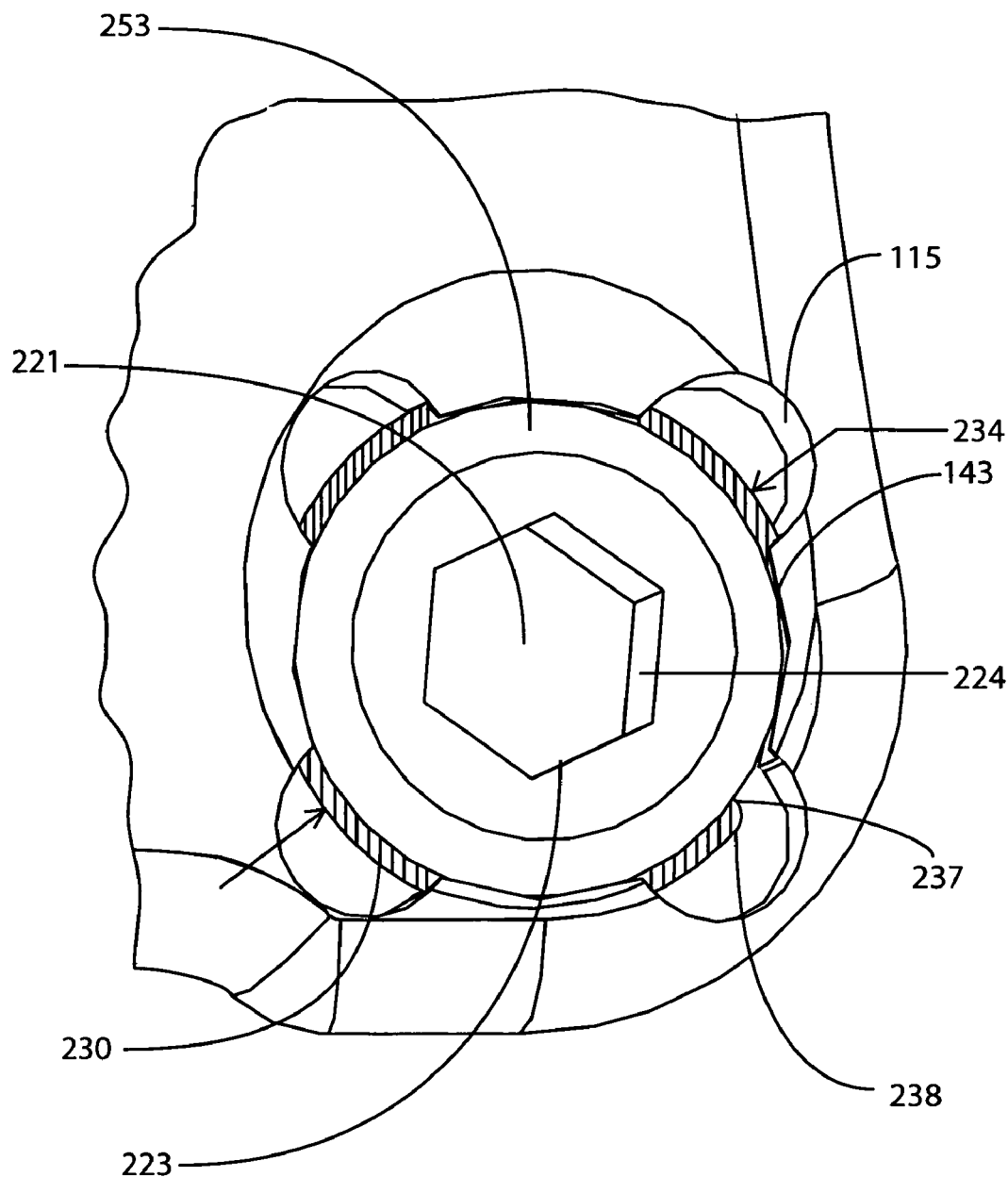
FIG. 6A is a close-up view showing the top of the bone plate, one fastener, and a retaining ring embodiment of the retaining member incorporated into the fastener head.
Figure 6B:
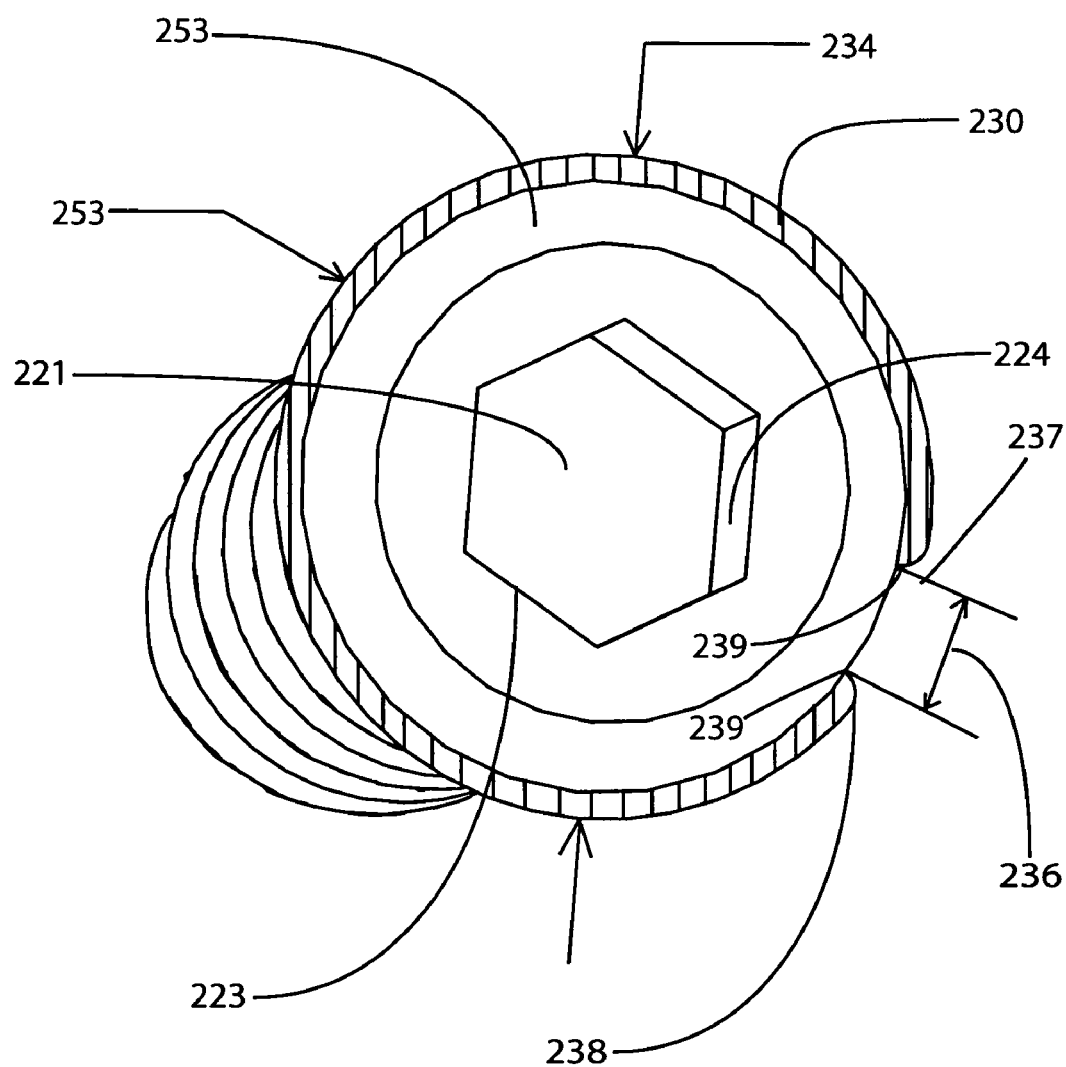
FIG. 6B is the same close-up view of FIG. 6A showing, for clarity, the top of the fastener and the retaining ring without the plate.

As shown in FIGS. 4B, 5A and 5B, and discussed above, the smallest functional diameter of the fastener-retaining passageway 110 is that of the bottom retainer diameter 147. The next largest functional diameter of the fastener-retaining passageway 110 is that of the capture lip diameter 143. The largest functional diameter of the fastener-retaining passageway 110 is the functional undercut diameter 144. Leading into the functional capture lip diameter 143 is a chamfer opening 148. The chamfer opening 148 tapers in toward the functional capture lip diameter 143 allowing the fastener head 250 to compress as it is driven into the fastener-retaining passageway 110. Thus the chamfer opening 148 provides a taper that constrains the retaining, ring 230 which elastically deforms as the fastener head 250 passes through the chamfer opening 148 from the top of the plate 130 through the fastener-retaining passageway capture lip 142 and into the functional undercut diameter 143. The fastener head 250 is partially decompressed as it is retained by the fastener-retaining passageway undercut 140. The elastic deformation and elastic recovery allows the fastener head 250 to lock into place and prevents the fastener 200 from backing out of the plate 100 after the fastener head 250 is retained by the fastener-retaining passageway undercut 140.

The amount that the fastener head 250 elastically recovers relative to the functional undercut diameter 144 is one factor that determines the fit between the plate 100 and the fastener 200. The greater the elastic recovery, the tighter the fit between the fastener head 250 and the fastener-retaining passageway undercut 140. To maintain a tight fit between the fastener head 250 and the fastener-retaining passageway undercut 140, the fastener head 250 is dimensioned to partially elastically decompress. This assures constant contact and friction between the fastener head 250 and the fastener-retaining passageway undercut 140.

Other factors that affect the fit between the fastener 200 and the plate 100 include the relative difference between the functional bottom restrainer diameter 147 of the plate 100 and a fastener shaft diameter 275. The closer that the dimension of the functional bottom restrainer diameter 147 is to the dimension of the fastener shaft diameter 275, the less toggle between the plate 100 and the fastener 200.

The radial elastic compression and recovery of the fastener head 250 is a function of both the material properties of the fastener head 250 and the structural design of the fastener head 250. The structural design and material properties of the fastener head 250 are variable depending on the radial elastic compression and recovery desired for the fastener head 250. If the elastic deformation is more a function of the material properties of the fastener head 250, the fastener head 250 can be fabricated from a biocompatible elastomeric polymer material such as polyurethane, delrin, polypropylene, PEEK or a biocompatible superelastic metallic alloy such as Nitinol. These highly elastic materials allow the fastener head 250 to elastically radially compress past the fastener-retaining passageway capture lip 142 and elastically recover to lock into place in the fastener-retaining passageway undercut 140.

If the fastener 200 is fabricated from a material that is not as highly elastic as those previously discussed, then the fastener head 250 geometry can be altered such that the required elastic radial deformation is still achieved. For example, the fastener head 250 can be designed to allow elastic radial deformation of the fastener head 250 by removing material to increase the bending displacement of the fastener head 250. Examples of materials that the plate 100 or the fastener 200 are made from include titanium, titanium alloys, cobalt-chrome alloys, stainless steel alloys, zirconium alloys, other biocompatible metal materials, biocompatible ceramics, biocompatible composites, and biocompatible polymers. For example, the fastener head 250 can be manufactured in a helical spring or spiral spring fabrication that allows the radial-compression and radial recovery of the fastener head 250. Or as shown in the embodiment of FIG. 4B, the fastener head 250 can be cut radially into wedge shaped slices 261 to allow each wedge shaped radial slice of the fastener head 250 to bend inward when radially compressed and elastically recover outward when the radial compression is removed. The wedge shaped slices 261 are formed by removing material in the shape of a flexion slot 262 between the wedge shaped slices 261. To reduce stress concentrations at the bottom of the flexion slots 262, and increase the flexibility of the wedge shaped slices 261, stress concentration reducing radii 263 are cut in the bottom of the flexion slots 262.

In addition to fabricating the fastener head 250 from a highly elastic material or designing the shape of the fastener head 250 such that it allows for radial compression and decompression, the fastener head elastic deformation member 254 can be a combination of both a radially elastic fastener structural design and the fastener head 250 partially or fully fabricated from a highly elastic material. Different portions of the fastener can be fabricated from different materials with elastic properties tailored to the function of a particular fastener feature. For example, the fastener head elastic deformation member 254 can be fabricated from highly elastic materials, while the fastener engager 270 is fabricated from less elastic materials.

In a second embodiment of the plate 100 and fastener 200 system, a retaining ring 230 is formed on the fastener head 250. As shown in FIG. 4F, a retaining ring 230 has a retaining ring top 231, a retaining ring underside 232, a retaining ring inner diameter 233, a retaining ring outer diameter 234, and a retaining ring bottom 235. To help facilitate radial elastic behavior, the retaining ring 230 has a retaining ring slot 237 with a retaining ring slot width 236 and a retaining ring slot wall 239 on both sides of the retaining ring slot 235. The larger the retaining ring slot width 236, the more the retaining ring 230 is able to radially compress before the retaining ring slot walls 239 interfere with each other, restricting further radial compression of the retaining ring 230. The retaining ring 230 can be fabricated from highly elastic biocompatible metallic materials such as Nitinol or biocompatible polymers including Delrin, high molecular weight polyethylene, PEEK, polysulfone and nylons. It can also be fabricated from traditional orthopedic metallic materials such as titanium, titanium alloys, stainless steel alloys, cobalt chrome alloys and zirconium alloys.

The fastener 200 has a fastener engager 270 that is adapted for fixation with the bone tissue by gripping onto and engaging the bone sections to be secured by the fastener 200 and plate 100 system. Although a screw type bone engaging member such as that of a engager thread 271 shown in FIG. 4 is the preferred embodiment of the fastener engager 270, other configurations of the fastener engager 270 such as barbs, press fits, radial expansion fits, multiple lead threads, and combinations of these and other tissue engagement can be configured as the fastener engager 270 and used interchangeably with the fastener engager 270 shown.

Figure 4C:
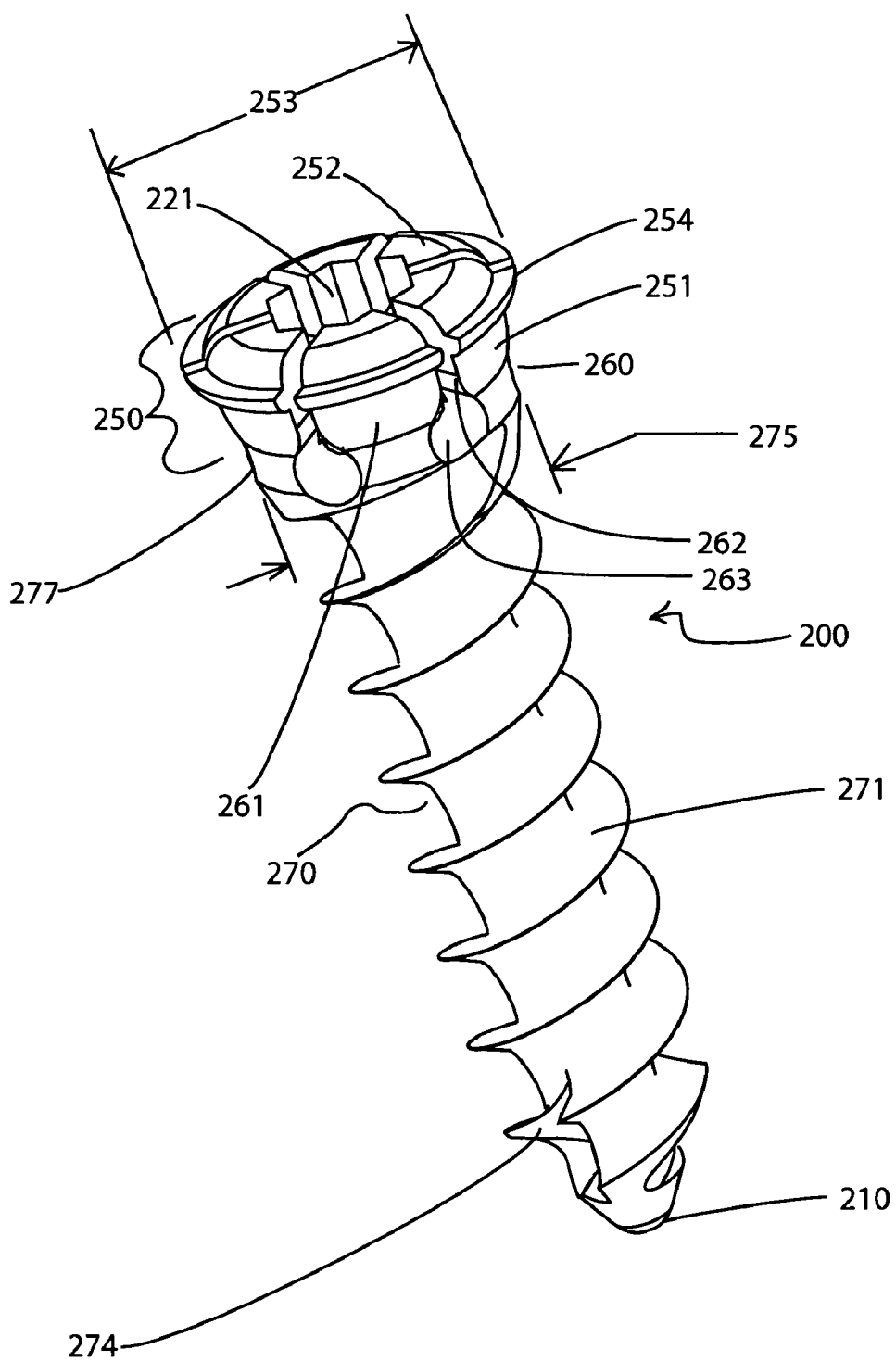
FIG. 4C is a perspective view of an embodiment of the fastener showing wedge shaped slices in the fastener head functioning as the radial elastic member.
Figure 4D:
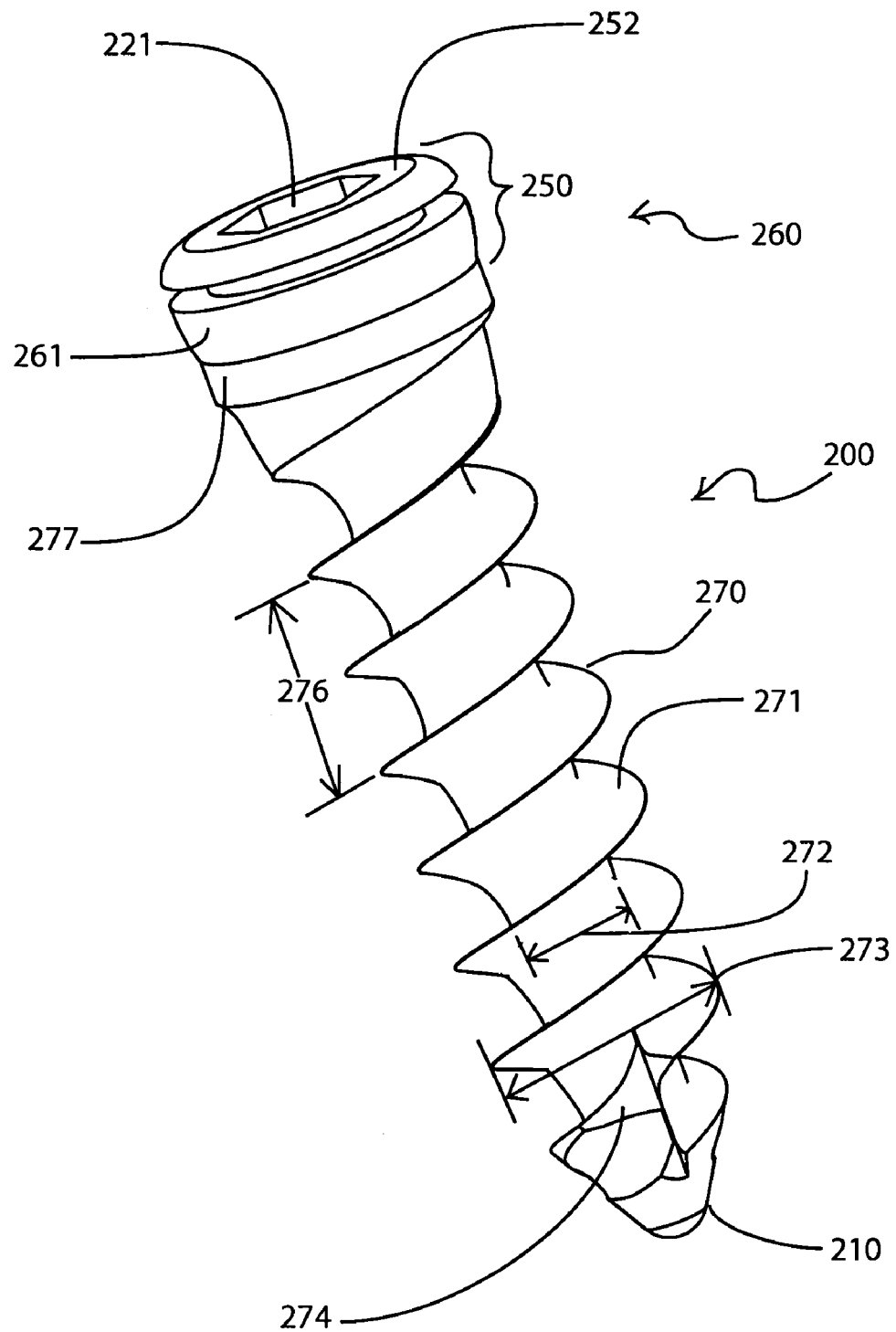
FIG. 4D is a perspective view of an embodiment of the part of the fastener which couples with a retaining ring (not shown) in its groove to function as a radial elastic member.
Figure 4E:
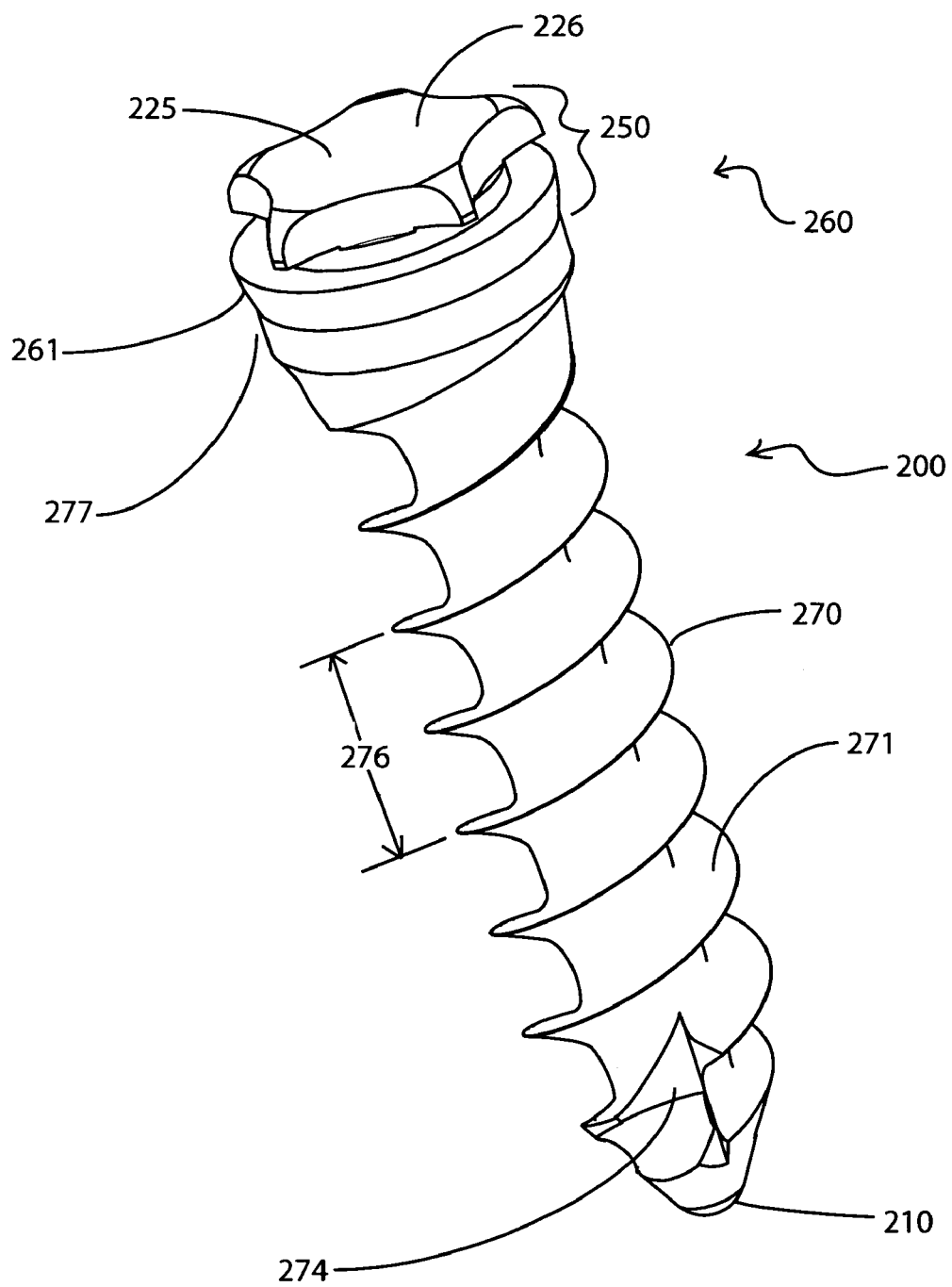
FIG. 4E is a perspective view of an embodiment of the fastener with an external protruding star shaped drive feature.
Figure 4F:
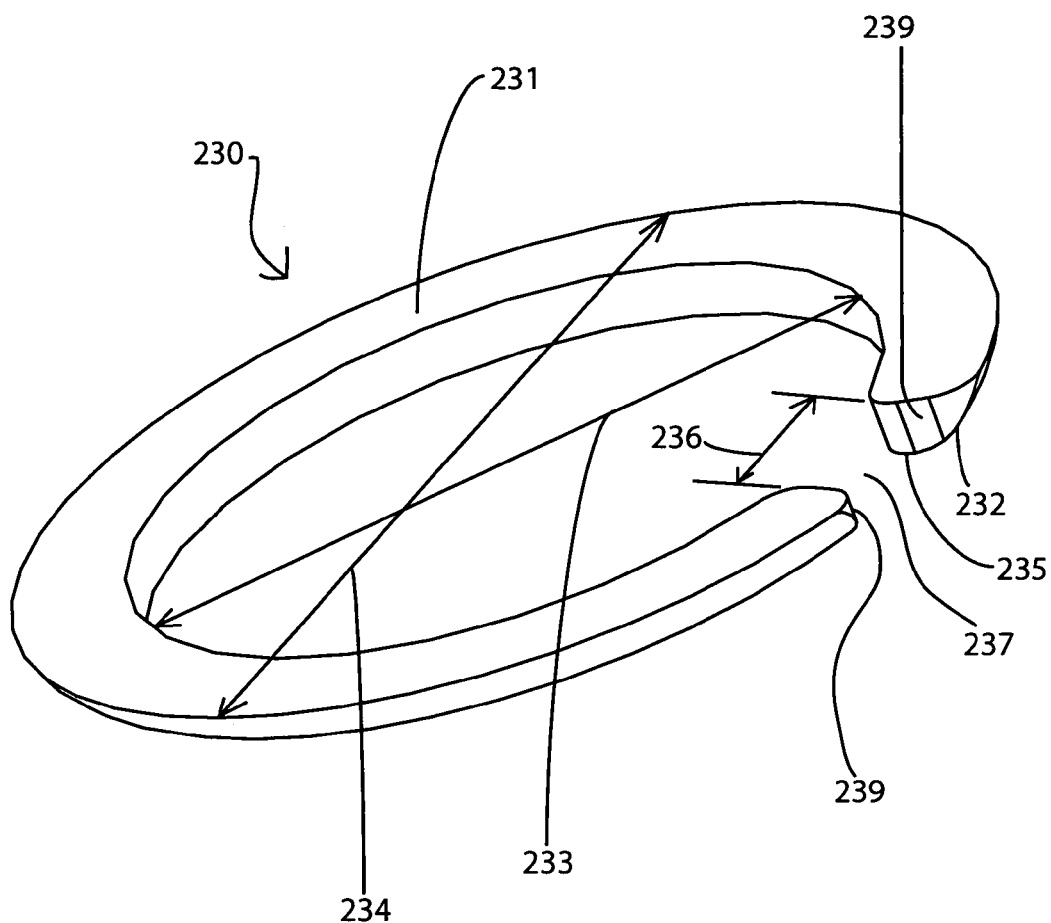
FIG. 4F is a perspective view of one embodiment of a retaining ring.

Referring to the embodiment of the fastener 200 shown in FIGS. 4C and 4D, the engager thread 271 that is shown represents one embodiment of the fastener engager 270. The engager thread 271 has an engager root diameter 272, an engager outside diameter 273 and an engager thread pitch 276. The engager thread 271 can be a single lead thread or a multiple lead thread. The particular thread pitch illustrated in FIGS. 4C, 4D and 4E are multiple lead threads. Multiple lead threads have multiple thread forms over a given thread engager length. This permits the surgeon to deliver the engager thread 271 with fewer turns than a traditional single lead thread. The engager thread 271 also has a fastener distal tip 210 positioned on the distal end of the fastener 200. Incorporated in the engager thread 271 is a cutting flute 274 that is shaped to displace tissue as the fastener engager 270 is driven into the bone segment. The cutting flute 274 allows the fastener 200 to be driven into place without prior tapping of the thread profile by a thread-taping instrument (not shown). The number of cutting flutes 274 positioned along the circumference of the distal tip 210 that are cut into the distal tip 210 depends on the desired self-cutting ability needed for the particular clinical indication. For example, two cutting flutes 274 are typically needed for starting the engager thread 271 in hard bone, while one cutting flute 274 may be all that is needed to start the engager thread 271 in less hard bone.

The embodiments of the fastener 200 shown in FIGS. 4A, 4C, 4D and 4E also have a fastener drive member 221 positioned on the fastener proximal end 260 that is on the opposite side of the fastener 200 from the fastener distal tip 210. In the embodiment shown in FIGS. 4A, 4C, and 4D the fastener non-circular drive member 223 is shown recessed into the fastener head 250. In these embodiments, the fastener non-circular drive member 223 is configured to accept a similarly shaped driver drive feature 540 on a driver 500. The driver drive feature 540 is used to drive the fastener 200. In this embodiment in which the fastener engager 270 is the engager thread 271, the driver 500 is rotated and screwing the fastener into bone. For other fasteners that use other engagement members such as barbs or radially expanding anchors, the fastener drive member 221 would be designed to accommodate the forces required to engage the fastener engager 270 into the bone and the plate 100. The particular fastener non-circular drive member 223 shown is a fastener hexagonal drive slot 224. However, the fastener non-circular drive member 223 slot can be shaped into other non-circular shapes such as a square, torques, star, or triangular.

As shown in FIG. 4E, the non-circular drive member 223 can also be configured the shape of an external protrusion non-circular drive member 225 and used to drive the fastener 200 into the plate 100 and the engager thread 271 into the bone segments. The external protrusion non-circular drive member 225 shown in FIG. 4E is a five point star drive member 226. However, the fastener non-circular drive member 223 protrusion can be shaped into other non-circular protrusions such as a hex, square, torques, pentagon, or triangular.

Referring to FIG. 3 which is a perspective view showing a bone plate and fasteners cut in a cross-section aligned with the center of the fasteners. The fasteners can be angled such that the distal tips 210 point towards each other as shown, or way from each other. They can also be angled in and out of the cross-sectional plane shown. The neutral position of this fastener angle is indicated in FIG. 3 by a symbol α and is dependent on the orientation of a central longitudinal axis of the fastener-retaining passageway 132 relative to a line tangent to the top of the plate 131. The angular play that the fastener 200 can rotate and toggle relative to the neutral position α is indicated in FIG. 3 by the symbol β. This angle β is three dimensional and conical passing into and out of the plane 600.

The configuration of the fastener-retaining passageway 110 in the plate 100 and the fastener head 250 allows for an angular play of β between the fastener 200 and the plate 100. Once the fastener head 250 is engaged with the plate 100, the fastener 200 can be oriented in a rotational position independently to any angle included in the angle β. The angular play β between the plate 100 and the fastener 200 is dependent upon the relative difference between the functional bottom retainer diameter 147 and the fastener shaft diameter 275. The amount of angulation between the long axis of the fastener 200 and an axis through the center of the fastener-retaining passageway 110 is between 0° and 15°. Generally, the more play between the plate 100 and the fastener 200, the more angular displacement.

In the first embodiment of the fastener 200 and plate variable angle system shown in FIG. 5A, the angular play β between of the fastener 200 and the plate 100 is structurally limited by the relative spacing between the functional bottom retainer diameter 147 and the fastener shaft diameter 275. The height of the undercut 140 is such that the retaining ring 230 stays within the undercut 140 regardless of where the fastener 200 is within its angular play of β. Consequently, the retaining ring 230 does not advance past the fastener-retaining passageway-undercut top 141 as the fastener is toggled.

Similarly, in the second embodiment of the fastener 200 and plate 100 variable angle system shown in FIG. 5B, the fixed fastener system, the fastener 200 and the plate 100 are structurally constrained by the relative spacing between the functional bottom retainer diameter 147 and the fastener shaft diameter 275. In the second embodiment, the retaining ring 230 is also in radial compression when it is within the fastener-retaining passageway undercut. Consequently, the retaining ring 230 in the second fixed angle embodiment of the fastener 200 does not advance past the fastener-retaining passageway undercut top 141 as the fastener is toggled. Also, because the retaining ring 230 is radially compressed and bias toward radial expansion, the retaining ring 230 is fully engaged in the undercut. This helps to better resist axial backout.

Figure 7:
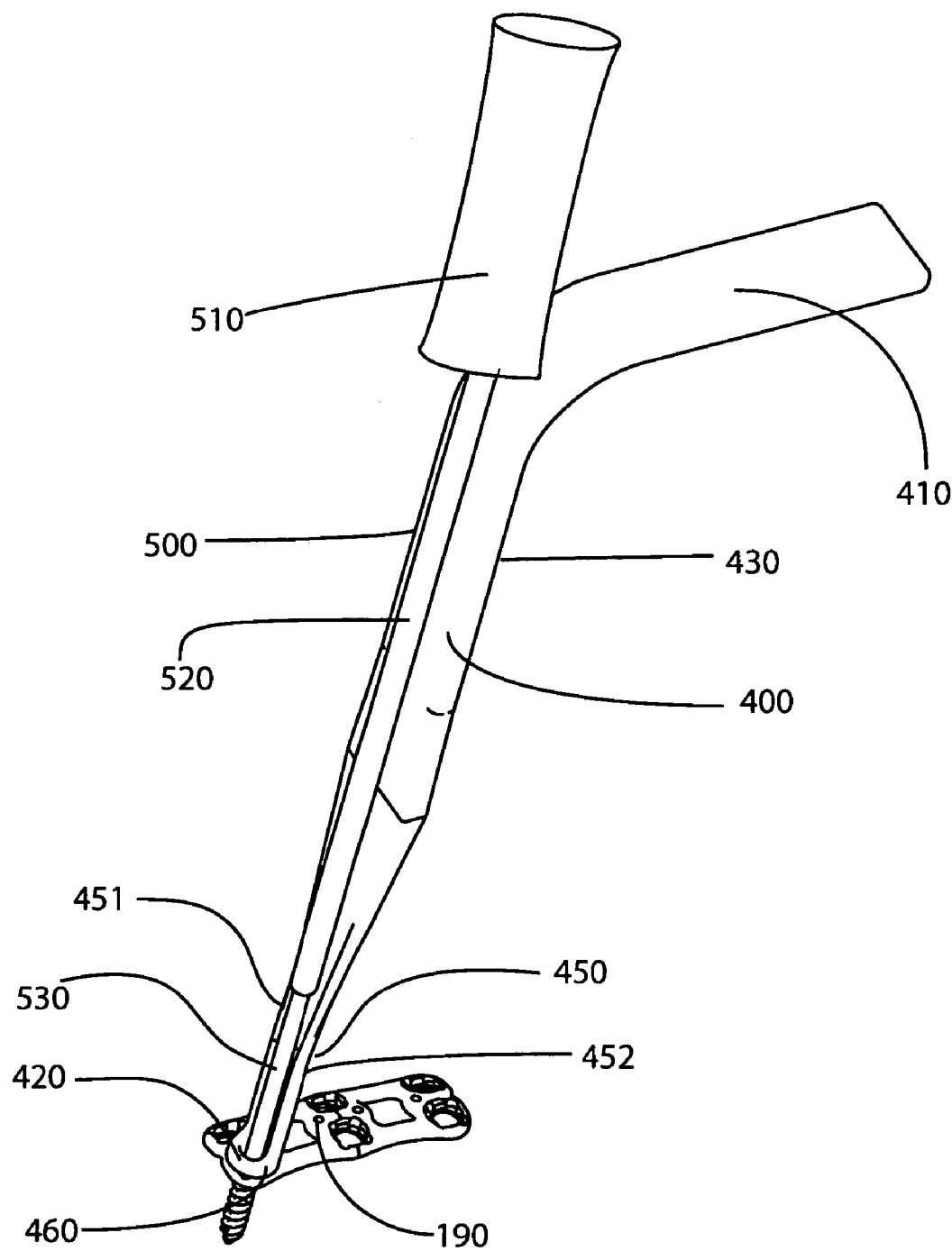
FIG. 7 is an isometric view of the plate and fastener system showing the removal tool positioned to radially compress the retaining ring and the fastener driver tool in place to remove the fastener.

Referring to FIG. 7, the plate 100 and fastener 200 implant system is shown with the associated instrumentation for removing the fastener 200 from the plate 100 and the bone segments. The driver 500 is shown attached to the fastener 200. A removal tool 400 is shown attached to the head of the fastener 200. The driver 500 has a driver handle 510 and a driver body 520 extending therefrom. The periphery of the driver handle 510 is shaped such to accept the surgeon's hand to facilitate driving and removal of the fastener 200 into and out of the plate 100 and bone. The driver body 520 is elongated to extend through the patients neck to the anterior cervical spine. Extending from the driver body 520 is a driver shaft 530. The driver shaft 530 may be the same diameter as the driver body 520 or it may be a different diameter. Its diameter is dependent upon the application of use and the surgical site to which the drive is inserted. When adapted for use in minimally invasive surgery with a minimal incision, the driver shaft 530 is typically smaller in diameter that the driver body 520 to allow the minimal space to be occupied by the driver 500.

Protruding from the driver shaft 530 is a driver drive feature 540. The driver drive feature 540 mates with the fastener drive member 221 in the fastener head 250 of the fastener 200. Hence, the shapes of the fastener drive member 221 and the driver drive feature 540 are similar and sized such that the male portion fits into the female portion. In the embodiments shown in FIGS. 1-7, the fastener head 250 is a female portion and receives the male portion driver 500 by engagement of the driver drive feature 540 in the fastener drive member 221. However, other embodiments of the driver drive feature 540 are internal female sockets that are designed to accept the male fastener drive member 221. The geometry of the driver drive feature 540 is similar to that of the fastener drive member 221 on the fastener head 250, but not necessarily exactly the same in shape. The shape needed to transmit the drive forces across mating surfaces need be present. In the embodiments of the driver drive feature 540 shown in FIGS. 1-7, the driver drive feature 540 is hexagonal shaped in geometry. However, other non-circular geometries such as a D shape, square, slotted circle, triangular, star, pentagon, or any other geometry suitable for transmitting the force or torque necessary to drive the fastener 200 are applicable shapes for the driver drive feature 540 and the fastener drive member 221.

The removal tool 400 shown in the embodiment depicted in FIGS. 7 through 11 has a handle 410 on the proximal end, a removal tool body 430 extending from the handle 410, and a removal tool small diameter shaft 450 extending from the removal tool body 430. The removal tool small diameter shaft 450 is dimensioned to fit into small incisions to access the plate 100 during the removal of the fastener 200 from the plate 100. The removal tool small diameter shaft 450 has an internal diameter 451 dimensioned to receive the driver shaft 530 and an outer diameter dimensioned to fit within the fastener removal incision (not shown). Adjacently connected and distal to the small diameter shaft 450 of the removal tool 400 is a prong support 460. The prong support 460 provides support for a set of prongs 440 that protrude from the prong support 460 in a pattern that is similar to the pattern of the retaining passageway access channels 115 in the plate 100. In this embodiment, the pattern for the prongs 440 and the retaining passageway access channels 115 are four evenly spaced along the circumference of the retaining passageway 110. Other patterns such as other multiples of prongs 440 and retaining passageway access channels 115 such as two, three, five, six or more can be incorporated into the design. In this embodiment, the prongs 440 and retaining passageway access channels 115 are approximately evenly spaced. This allows the removal tool 400 to fit through the plate 100 in multiple orientations around the periphery of the retaining passageway 110. However in other embodiments, the distance between prongs 440 can be non-evenly spaced and the distance between the retaining passageway access channels 115 can be non-evenly spaced. This could result in specified orientations between the removal tool 400 and the plate 100. Also the number of retaining passageway access channels 115 in the plate 100 may be more than the number of prongs 440 on the removal tool.

Figure 8:
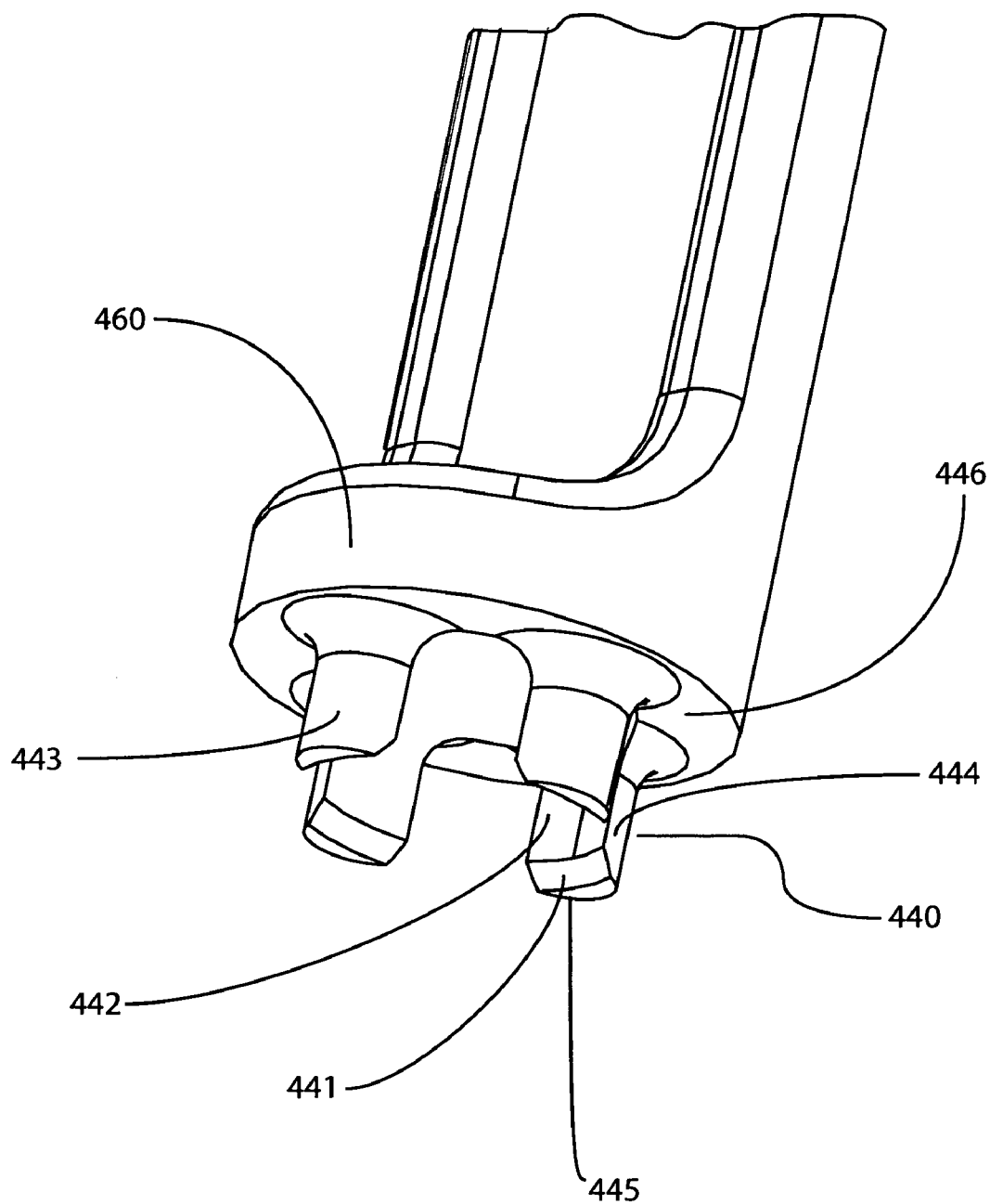
FIG. 8 is an isometric detail view of a distal end of one embodiment of the removal tool showing the prongs that radially compress the radially elastic compressive member of the fastener.

As shown in FIG. 8, the prongs 440 comprise of a prong body 444 protruding from the prong support, a prong internal surface 442 facing the center of the removal tool 400, a prong external surface 443 facing the outside of the removal tool 400, and a prong distal tip 445 that faces the distal end of the removal tool 400. A prong fillet 446 comprises transitional material between the prong support 460 and the prongs 440. The prong fillet 446 also provides additional stability to the prong 440.

A prong lead in chamfer 441 is adjacent to the distal end of the internal surface 442. The prong lead-in chamfer 441 slopes outwardly from the internal surface 442 to the distal tip 445.

The prongs 440 shown in FIGS. 7 through 11B are stationary prongs that do not articulate or move with respect to the prong support 460. Another embodiment of the removal tool 400 is comprised of prongs that contain kinematic linkages that allow the prongs to move with respect to the prong support 460 in such a way as to radially compress the retaining ring 230 during fastener 200 disengagement from the plate 100.

Figure 9:
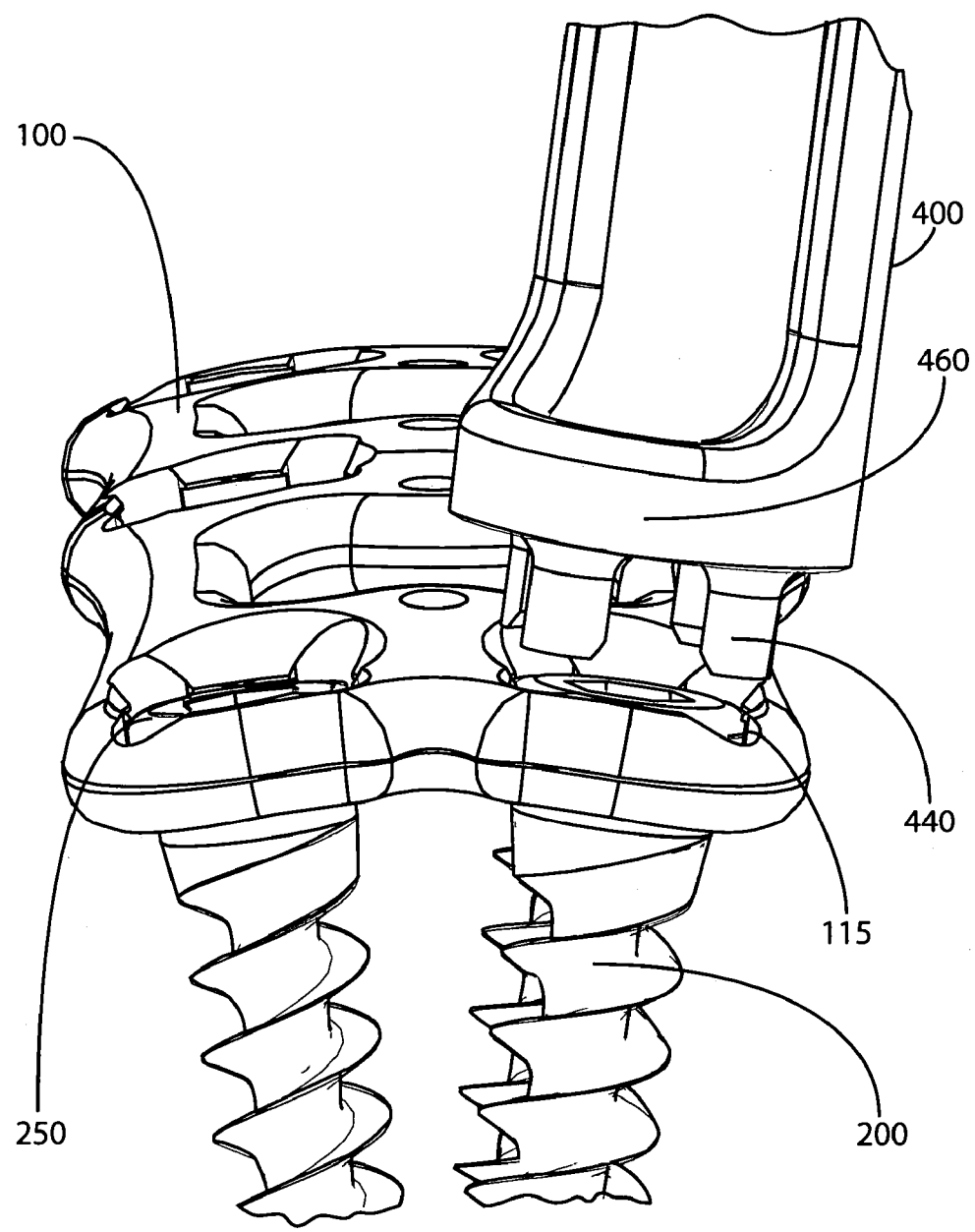
FIG. 9 is an isometric detail view of the distal end of the removal tool prior to being positioned into the access channels in the retaining passageway in the plate before engagement with the fastener and radial compression of the radially elastic compressive member of the fastener.
Figure 10:
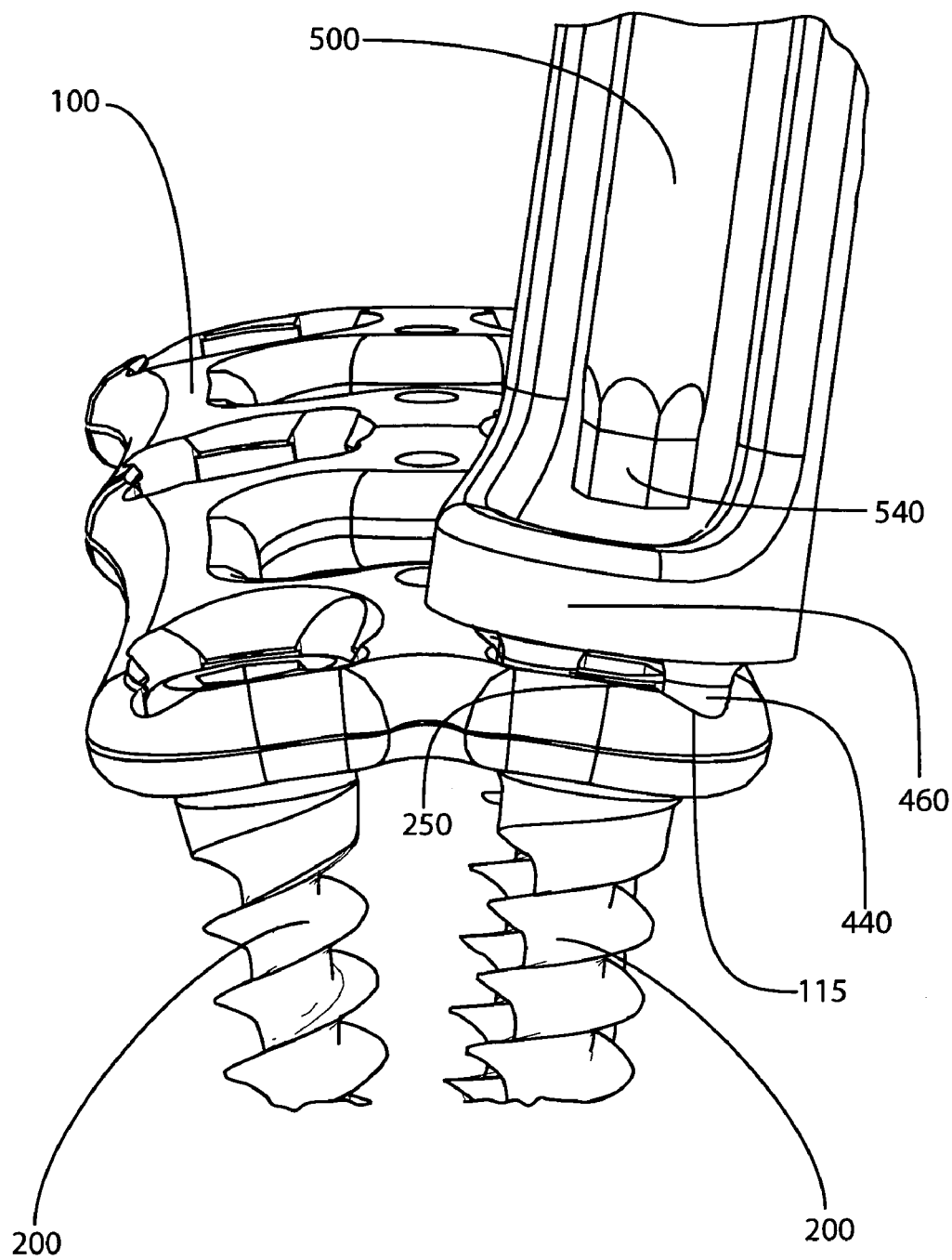
FIG. 10 is an isometric detail view of the removal tool engaged with the head of the fastener holding the radially elastic compressible member in radial compression while the driver tool is being moved into position to remove the fastener from the plate.
Figure 11A:
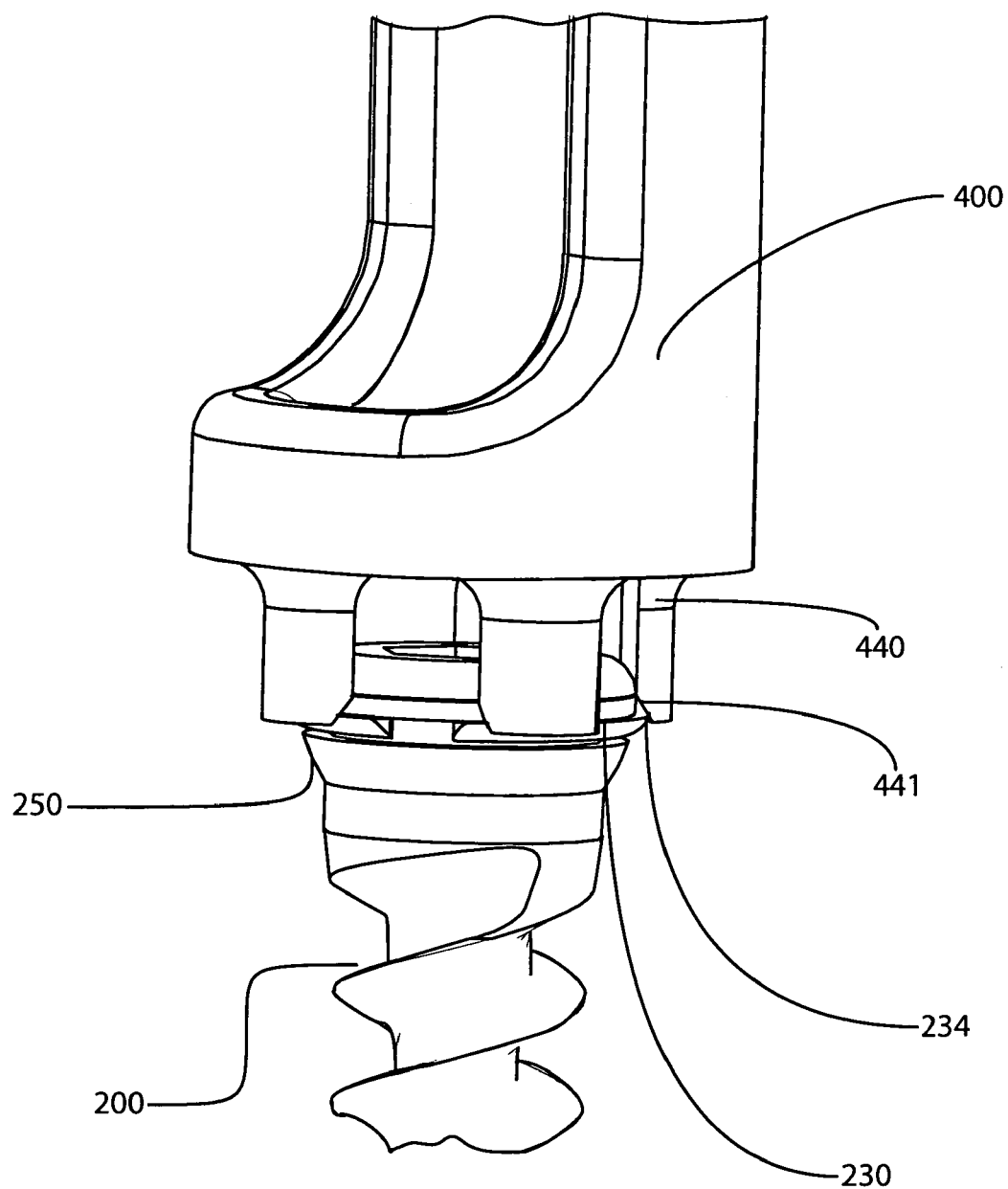
FIG. 11A is an isometric detail view of a removal tool prior to engagement with the head of the fastener and radial compression of the retaining ring, the plate is removed from the view for clarity.
Figure 11B:
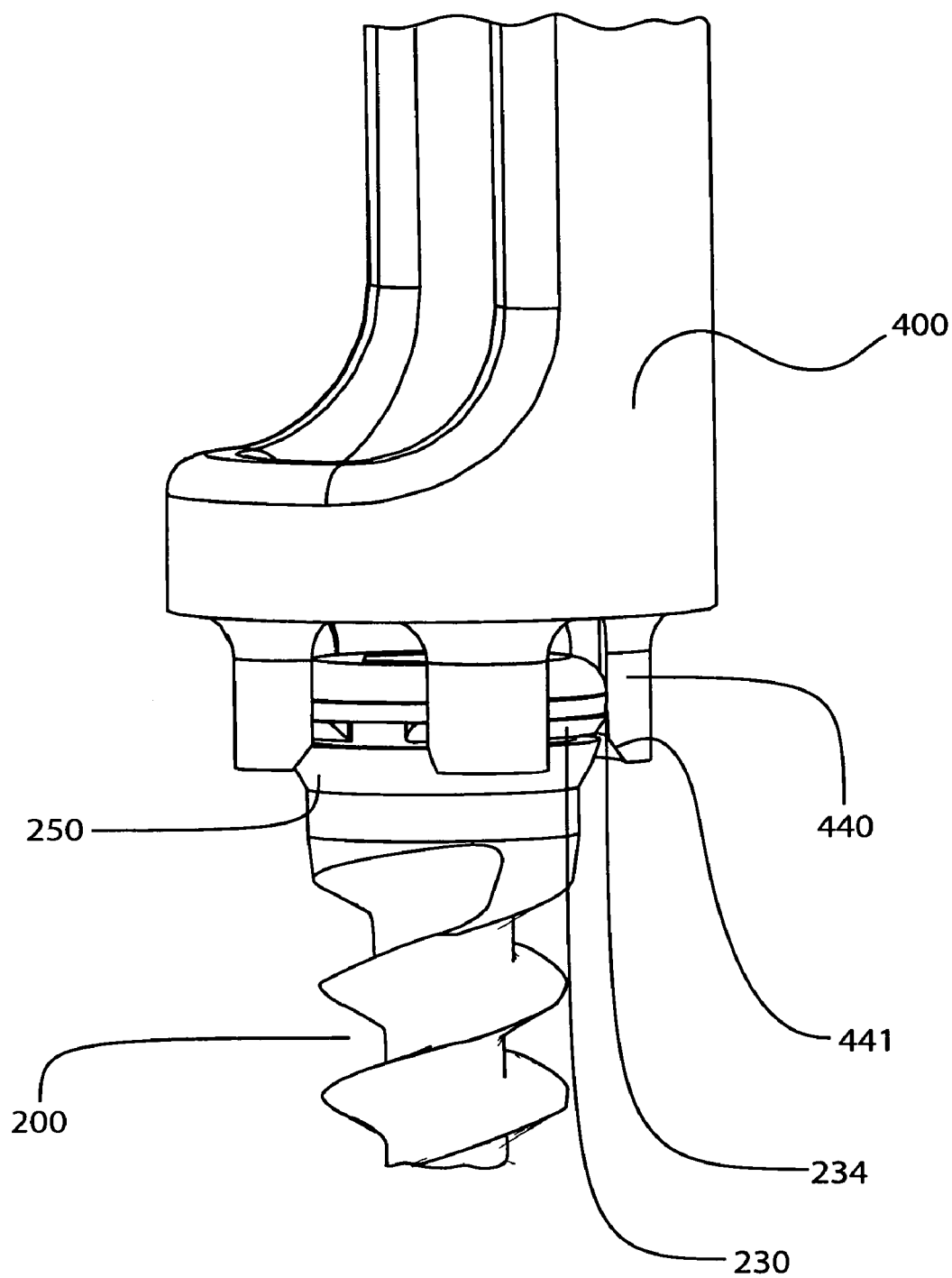
FIG. 11B is an isometric detail view of a removal tool engaged with the head of the fastener holding the head in radial compression with the plate removed from the view for clarity.

Referring to FIG. 9, the prongs 440 of the removal tool 400 are being positioned into the fastener-retaining passageway access channels 115 in the plate 100. As shown in FIG. 10, as the prongs 440 are positioned in the fastener-retaining passageway access channels 115, they engage with the fastener head to radially compress the retaining ring 230. This is shown more clearly in FIGS. 11A and 11B in which the plate 100 is removed from view for visual clarity. As shown in FIG. 11A, the chamfers 441 on the prongs 440 push against the retaining ring outer diameter 234 as the removal tool 400 is advanced longitudinally towards the fastener 200. As shown in FIG. 11B, the retaining ring 230 is radially compressed by the chamfers 441 on the prongs 440 until the retaining ring outer diameter 234 is equal to or smaller than the diameter needed to clear the functional capture lip diameter 143.

While the present invention has been disclosed in its preferred form, the specific embodiments thereof as disclosed and illustrated herein are not to be considered in a limiting sense, as numerous variations are possible. The invention may be embodied in other specific forms without departing from its spirit or essential characteristics. The described embodiments of the plate and fastener system are to be considered in all respects only as illustrative and not restrictive. No single feature, function, element or property of the disclosed embodiments is essential. The scope of the invention is, therefore, indicated by the appended claims rather than by the foregoing description. The following claims define certain combinations and subcombinations that are regarded as novel and non-obvious. Other combinations and subcombinations of features, functions, elements and/or properties may be claimed through amendment of the present claims or presentation of new claims in this or related applications. Such claims, whether they are broader, narrower or equal in scope to the original claims, are also regarded as included within the subject matter of applicant's invention. All changes that come within the meaning and range of equivalency of the claims are to be embraced within their scope.

The invention claimed is:

1. A bone plating system comprising:
   a bone plate having a top portion, a bottom portion, and an interior middle portion extending therebetween, the interior middle portion bounding a fastener-retaining passageway extending between the top portion and the bottom portion, the fastener-retaining passageway comprising:
      an upper portion having an inwardly projecting capture lip formed thereat, the capture lip having a first diameter;
      a lower undercut portion with a cross sectional shape perpendicular to an axis of the passageway, the cross sectional shape having a second diameter at a circular periphery thereof that is larger than the first diameter; and
      at least one access channel extending through the capture lip, said at least one access channel intersecting a circular periphery of the capture lip so as to communicate with the lower portion; and
   a fastener comprising:
      a shaft;
      a fastener engager extending from, disposed on or coupled with the shaft for engaging bone; and
      a head mounted on the shaft, the head having a radially elastic member.

2. A bone plating system as in claim 1 wherein the fastener engager comprises a thread.

3. A bone plating system as in claim 1 wherein the fastener engager comprises a non-threaded engager.

4. A bone plating system as in claim 1 wherein the head comprises:
   a peripheral groove at least partially encircling the head or the shaft; and
   wherein the radially elastic member comprises a retention ring at least partially disposed within the peripheral groove, the retention ring being resiliently movable between a constricted state and a free state.

5. A bone plating system as in claim 1 wherein the radially elastic member comprises:
   a fastener head fabricated from a highly elastic material allowing the fastener head to be resiliently movable between a radially constricted state and a free state.

6. A bone plating system as in claim 5 wherein the highly elastic material is Nitinol.

7. A bone plating system as in claim 5 wherein the highly elastic material is a biocompatible polymer.

8. A bone plating system as in claim 1 wherein the radially elastic member comprises:
   a plurality of radially elastic wedge shaped slices spaced radially about the head, the wedge shaped slices being resiliently movable between a constricted state and a free state.

9. A bone plating system as in claim 1 wherein the fastener has a drive member that is selectively received by a driver to guide and position the fastener.

10. A bone plating system comprising:
    a bone plate having a top, a bottom, and an interior portion bounding a retaining passageway extending therebetween, the retaining passageway comprising:
       an upper portion having an inwardly projecting capture lip formed thereat, the capture lip having a first diameter;
       a middle portion having a second diameter that is larger than the first diameter; and
       a plurality of spaced apart access channels extending through the capture lip so as to communicate with the middle portion;
    a fastener having peripheral groove at least partially encircling the fastener;
    a retention ring at least partially disposed within the peripheral groove, the retention ring being resiliently movable between a constricted state and a free state, the fastener being configured to pass through the passageway of the bone plate so that the retention ring is disposed within the passageway;
    a removal tool comprising a plurality of spaced apart prongs, the prongs being configured to be selectively received within the plurality of spaced apart access channels so as to radially inwardly constrict the retention ring when the retention ring is disposed within the passageway of the bone plate.

11. A bone plating system as in claim 10 wherein the fastener further comprises a thread configured to engage bone.

12. A bone plating system as in claim 10 wherein the fastener further comprises a non-threaded fastener engager configured to engage bone.

13. A bone plating system as in claim 10 wherein the fastener has a drive member that is selectively received by a driver to guide and position the fastener.

* * * * *

UNITED STATES PATENT AND TRADEMARK OFFICE
CERTIFICATE OF CORRECTION

| | | |
|---|---|---|
| PATENT NO. | : 7,309,340 B2 | Page 1 of 1 |
| APPLICATION NO. | : 10/601177 | |
| DATED | : December 18, 2007 | |
| INVENTOR(S) | : T. Wade Fallin et al. | |

It is certified that error appears in the above-identified patent and that said Letters Patent is hereby corrected as shown below:

Column 2, Line 40: Delete Hyphen between "by" and "either"
Column 3, Line 62: Delete Hyphen after "elastic"
Column 6, Line 11: Delete Hyphen after "restricted"
Column 11, Line 26: Delete "of" after "between"
Column 12, Line 1: Delete "that" ADD --than--

Signed and Sealed this

Sixteenth Day of September, 2008

JON W. DUDAS
*Director of the United States Patent and Trademark Office*